United States Patent
Stanley et al.

(10) Patent No.: US 12,096,838 B2
(45) Date of Patent: Sep. 24, 2024

(54) METHOD OF MAKING APPLICATOR WITH PRECISION EYE OPENING

(71) Applicant: The Procter & Gamble Company, Cincinnati, OH (US)

(72) Inventors: Scott Kendyl Stanley, Mason, OH (US); Andrew Paul Rapach, Fairfield, OH (US); Jill Marlene Orr, Sharonville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1388 days.

(21) Appl. No.: 16/594,148

(22) Filed: Oct. 7, 2019

(65) Prior Publication Data

US 2021/0100992 A1  Apr. 8, 2021

(51) Int. Cl.
*A45D 44/00* (2006.01)
*A61M 35/00* (2006.01)
*G06F 18/2413* (2023.01)
*G06T 15/10* (2011.01)
*G06T 17/00* (2006.01)
(Continued)

(52) U.S. Cl.
CPC ........... *A45D 44/002* (2013.01); *A61M 35/10* (2019.05); *G06F 18/24133* (2023.01); *G06T 15/10* (2013.01); *G06T 17/00* (2013.01); *G06V 10/44* (2022.01); *G06V 10/764* (2022.01); *G06V 40/168* (2022.01); *G06V 40/171* (2022.01);
(Continued)

(58) Field of Classification Search
CPC ................ A45D 44/002; A61M 35/10; A61M 2202/0208; A61M 2207/00; A61M 2210/0612; G06F 18/24133; G06T 15/10; G06T 17/00; G06V 10/44; G06V 10/764; G06V 40/168; G06V 40/171
USPC .......................................................... 700/98
See application file for complete search history.

(56) References Cited

U.S. PATENT DOCUMENTS 3,154,070 A    10/1964   Renee
3,499,446 A    3/1970   Tsuneizumi
(Continued)

FOREIGN PATENT DOCUMENTS

CN    203400409 U    1/2014
CN    204016893 U    12/2014
(Continued)

OTHER PUBLICATIONS

International Search Report and Written Opinion, PCT/US2019/054992, dated Jan. 10, 2020, 13 pgs.

*Primary Examiner* — Chun Cao
*Assistant Examiner* — Michael Tang
(74) *Attorney, Agent, or Firm* — Kathleen Y. Carter; Sarah M. DeCristofaro; David Michael Weirich

(57) ABSTRACT

A method of making a face mask for a face of a human user can include determining a lower eye region bound and determining an upper eye region bound by locating an upper bound of the eyeball as determined by a peak point of an arc of concavity in an upper eyelid of the at least one eye when the eye is closed. The method can also include setting a first anchor point about 0 mm to about 10 mm below the lower eye region bound, and setting a second anchor point about 0 mm to about 10 mm above the upper eye region bound; and defining at least one eye opening for a face mask having first edge that intersects the first anchor point and a second edge that intersects the second anchor point.

20 Claims, 16 Drawing Sheets

(51) Int. Cl.
  *G06V 10/44* (2022.01)
  *G06V 10/764* (2022.01)
  *G06V 40/16* (2022.01)
(52) U.S. Cl.
  CPC . *A61M 2202/0208* (2013.01); *A61M 2207/00* (2013.01); *A61M 2210/0612* (2013.01)

(56) References Cited

U.S. PATENT DOCUMENTS

| | | | |
|---|---|---|---|
| 4,847,921 A * | 7/1989 | Leutholt | A63B 71/10 |
| | | | 2/206 |
| 4,886,079 A | 12/1989 | Mooney | |
| 5,343,479 A | 8/1994 | Kiyozuka | |
| 5,576,778 A * | 11/1996 | Fujie | G02C 13/003 |
| | | | 351/159.75 |
| 5,765,231 A | 6/1998 | Leonard | |
| 5,832,918 A | 11/1998 | Pantino | |
| 5,913,883 A | 6/1999 | Alexander | |
| 6,001,380 A | 12/1999 | Smith | |
| 6,530,379 B2 | 3/2003 | Iosilevich | |
| 6,728,589 B1 | 4/2004 | Delache | |
| 7,340,316 B2 | 3/2008 | Spaeth | |
| 7,904,193 B2 | 3/2011 | Janbakhsh | |
| 8,218,862 B2 | 7/2012 | Demirli | |
| 8,254,637 B2 | 8/2012 | Abourizk | |
| 8,358,348 B2 | 1/2013 | Mohammadi | |
| 8,372,130 B2 | 2/2013 | Young | |
| 8,425,477 B2 | 4/2013 | Mou | |
| 8,464,732 B2 | 6/2013 | Wong | |
| 8,540,445 B2 | 9/2013 | Omoto | |
| 8,695,610 B2 | 4/2014 | Samain | |
| 8,780,975 B2 | 7/2014 | Gadat | |
| 8,874,251 B2 | 10/2014 | Thornton | |
| 9,058,765 B1 * | 6/2015 | Mallick | G06Q 30/0256 |
| 9,296,129 B2 | 3/2016 | Pallari | |
| 9,498,593 B2 | 11/2016 | Karpas | |
| 9,572,402 B2 | 2/2017 | Jarvis | |
| 2003/0167556 A1 | 9/2003 | Kelley | |
| 2006/0104931 A1 | 5/2006 | Fukutome | |
| 2006/0147119 A1 * | 7/2006 | Takano | A61K 8/02 |
| | | | 705/26.1 |
| 2008/0014231 A1 | 1/2008 | Okano | |
| 2008/0058915 A1 | 3/2008 | Chang | |
| 2008/0069845 A1 | 3/2008 | Makihara | |
| 2009/0267261 A1 | 10/2009 | Mark | |
| 2011/0271973 A1 * | 11/2011 | Iwagaki | A61K 8/731 |
| | | | 132/200 |
| 2012/0192884 A1 | 8/2012 | Nasu et al. | |
| 2012/0305003 A1 | 12/2012 | Mark | |
| 2013/0174862 A1 | 7/2013 | Samain | |
| 2014/0261430 A1 | 9/2014 | Davis | |
| 2014/0352134 A1 | 12/2014 | Ho | |
| 2015/0035200 A1 | 2/2015 | Karpas | |
| 2015/0042762 A1 | 2/2015 | Kim | |
| 2015/0262403 A1 * | 9/2015 | Yamanashi | G06T 7/73 |
| | | | 345/634 |
| 2015/0265794 A1 | 9/2015 | De Kruyff | |
| 2016/0022014 A1 | 1/2016 | Ajiki | |
| 2016/0162965 A1 * | 6/2016 | Lee | G02C 13/003 |
| | | | 705/26.5 |
| 2016/0316892 A1 | 11/2016 | Giron | |
| 2017/0086566 A1 | 3/2017 | Stanley et al. | |
| 2017/0209720 A1 * | 7/2017 | Mingo | A62B 23/025 |

FOREIGN PATENT DOCUMENTS

| | | | |
|---|---|---|---|
| CN | 104476772 A | | 4/2015 |
| CN | 104721061 | | 6/2015 |
| CN | 204709438 U | * | 10/2015 |
| CN | 204869675 U | | 12/2015 |
| CN | 207400911 U | * | 5/2018 |
| DE | 102004009971 A1 | | 9/2005 |
| DE | 102005042911 A1 | | 3/2007 |
| JP | H03137239 A | | 6/1991 |
| JP | 11169231 A | | 6/1999 |
| JP | 2000031292 A | | 1/2000 |
| JP | 2000107683 A | | 4/2000 |
| JP | 3144385 U3 | | 8/2008 |
| JP | 2018061670 A | | 4/2018 |
| JP | 2018117834 A | | 8/2018 |
| KR | 20040016534 A | | 2/2004 |
| KR | 200416534 Y1 | | 5/2006 |
| KR | 20060064553 A | * | 6/2006 |
| KR | 20170078416 A | | 7/2017 |
| KR | 101867564 B1 | * | 7/2018 |
| TW | M559174 U | | 5/2018 |
| WO | WO2007123380 A1 | | 11/2007 |
| WO | WO201178038 A1 | | 6/2011 |
| WO | WO2013050524 A1 | | 4/2013 |
| WO | WO2013108918 A1 | | 7/2013 |
| WO | WO201403183 A1 | | 1/2014 |

* cited by examiner

METHOD OF MAKING APPLICATOR WITH PRECISION EYE OPENING

FIELD OF THE DISCLOSURE

The disclosure relates to masks having custom openings and methods of creating mask having custom openings defined therein.

BACKGROUND OF THE DISCLOSURE

Agents for affecting target structures are well known. Temperature affects may be induced by the application of hot or cold agents to the target. The appearance of a target may be affected by cosmetic and decorative agents. Electric current, voltages, and electric and magnetic fields may be applied to a target using local applicators. For biological targets, surface properties may be impacted by the use of topical application of moisturizers, medicaments and other treatment actives.

The effectiveness of the active agent may be impacted by the nature of the applicator available to facilitate the interaction of the active agent with the target structure. Typical applicators are less than precise with respect to their conformance to the target structure and the use of one-size, or a few sizes, fits all tends to compromise the actual performance of the active agent. In particular, conventional one-size fits all applicators for facial products, for example, typically have universally large eye and lip openings to accommodate variations in user's features. As a result, such applicators are ineffective at applying an active agent in the region of the eye or the lips in many individuals. Additionally, given the general poor fit and registration of conventional applicators on the face, alignment of eye and lip openings can be particularly difficult and lead to discomfort by the user.

SUMMARY OF THE DISCLOSURE

In accordance with embodiments, applicators having custom sized openings and methods of making the same can include applicators with agents for affecting target structures, for example, beauty masks.

In accordance with embodiments, a method of making a face mask for a face of a human user can include determining a lower eye region bound. For example, the lower eye region bound can be determined by locating a position of one or more of a lowest extent of one or more lower eyelashes of the at least one eye when the eye is open, a lower bound of the eyeball as determined by a peak point of an arc of concavity in the lower eyelid of the at least one eye when the eye is closed, and a lowest extent of one or more upper eyelashes of the at least one eye when the eye is closed. The method can further include determining an upper eye region bound. For example, the upper eye region bound can be determined by locating an upper bound of the eyeball as determined by a peak point of an arc of concavity in an upper eyelid region of the at least one eye when the eye is closed. The eye height is defined by the distance between the lower eye region bound and the upper eye region bound. The method also includes defining the at least one eye opening such that, when the mask is fitted to the face, the first edge is disposed 0 mm to about 10 mm below the lower eye region bound and the second edge is disposed 0 mm to about 10 mm above the upper eye region bound. The method can also include creating the face mask having the at least one eye opening.

In accordance with embodiments, a method of making a face mask for a face of a human user can include determining a lower eye region bound. For example, the lower eye region bound can be determine by locating a position of one or more of a lowest extent of one or more lower eyelashes of the at least one eye when the eye is open, a lower bound of the eyeball as determined by a peak point of an arc of concavity in the lower eyelid of the at least one eye when the eye is closed, and a lowest extent of one or more upper eyelashes of the at least one eye when the eye is closed. The method can further include determining an upper eye region bound. For example, the upper eye region by can be determined by locating an upper bound of the eyeball as determined by a peak point of an arc of concavity in an upper eyelid region of the at least one eye when the eye is closed. The method can also include setting a first anchor point about 0 mm to about 10 mm below the lower eye region bound, and setting a second anchor point about 0 mm to about 10 mm above the upper eye region bound. The method also includes defining at least one eye opening for a face mask having first edge that intersects the first anchor point and a second edge that intersects the second anchor point. The method can further include creating the face mask having the at least one eye opening. In embodiments, the first and/or the second edge can be curved.

In accordance with embodiments, a method of making a face mask for a face of a human user can include a) determining on a digital geometric representation of the face including at least one eye each of a position of a medial canthus, a position of a lateral canthus, a lower eye region bound, and an upper eye region bound. For example, the lower eye region bound can be defined by one or more of a lowest extent of one or more lower eyelashes of the at least one eye when the eye is open, a lower bound of the eyeball as determined by a peak point of an arc of concavity in the lower eyelid region of the at least one eye when the eye is closed, and a lowest extent of one or more upper eyelashes of the at least one eye when the eye is closed. For example, the upper eye region bound can be defined by upper bound of the eyeball as determined by a peak point of an arc of concavity in an upper eyelid of the at least one eye when the eye is closed. The method can further include b) setting a first anchor point about 1 mm to about 10 mm outboard (taking the eye center as reference point) from the medial canthus, c) setting a second anchor point about 1 mm to about 10 mm outboard from the lateral canthus, d) setting a third anchor point spaced about 0 mm to about 10 mm below lower eye region bound, and e) setting a fourth anchor point spaced about 0 mm to about 10 mm above the upper eye region bound. The method can also include f) defining at least one eye opening having a first edge defined by a first curve connecting the first, third, and second anchor points, and a second edge defined by a second curve connecting the first, fourth, and second anchor points. The method can include creating the face mask having the defined at least one eye opening.

In any of the foregoing methods or methods disclosed herein, two eye openings can be defined, repeating the steps of the methods for each eye.

In embodiments, a method can include or further include determining a position of an outermost edge of each of first and second nostrils, setting a first nose anchor point about 0 mm to about 10 mm from the outermost edge of the first nostril, setting a second nose anchor point about 0 mm to about 10 mm from the outermost edge of the second nostril, and defining a nose opening having side edges that intersect with the first and second nose anchor points. In various embodiments, the method can include or further includes determining a position of the base of the columella, determining a position of the tip of the nose, setting a third nose anchor point about 0 mm to about 10 mm from the position of the base of the columella and a fourth nose anchor point 0 mm to about 10 mm from the position of the tip of the nose, and defining a nose opening to have a circumferential edges that intersects with each of the first, second, third, and fourth anchor points. In embodiments, a method can include or further includes determining an uppermost point of at least one of the first and second nostrils; setting a fifth nose anchor point about 0 to about 10 mm from the base of the columella, setting a sixth nose anchor point about 0 to about 10 mm from one of the uppermost points of the first and second nostrils and defining the mask to have a nose opening with top and bottom edges that intersect with the fifth and sixth nose anchor points. In various embodiments, the fifth nose anchor point can be the uppermost one of the uppermost point of the first and second nostrils. In various embodiments, the fifth nose anchor point can be the uppermost point of the first nostril and a fifth nose anchor point can be defined at the upper most point of the second nostril. In various embodiments, the nose opening can be defined such that the edges of the opening interest with two anchor points, three anchor points, four anchor points, five anchor points, six anchor points, or more.

In accordance with embodiments, method can include or further include defining a mouth opening. The method can include determining a position of an upper point of the vermillion border and determining a position of a lower point of the vermillion border. The method can further include setting a first lip anchor point about 0 mm to about 10 mm from the upper point of the vermillion border, and setting a second lip anchor point about 0 mm to about 10 mm from the lower point of the vermillion border. The method can also include and defining a mouth opening having a first edge that intersects with the first lip anchor point and a second edge that intersects with the second lip anchor point. In various embodiments, the method can include or further include determining positions of each of the first and second corners of the mouth, setting a third lip anchor point about 0 mm to about 10 mm from the first corner, setting a fourth lip anchor point about 0 mm to about 10 mm from the second corner, and defining a mouth opening having a first edge that intersects the first, third, and fourth anchor points, and a second edge that intersects the second, third, and fourth anchor points.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE DISCLOSURE

In one aspect the face mask comprises at least one opening having a shape determined according to a digital geometric representation, or other created digital geometric representation of a target structure.

As used herein the term flexible means that a three-dimensional geometry of an element or the applicator in its entirety may be altered without any permanent deformation of the element's geometry. Applicator is also interchangeable used herein with "face mask" or "mask."

Figure 1A:
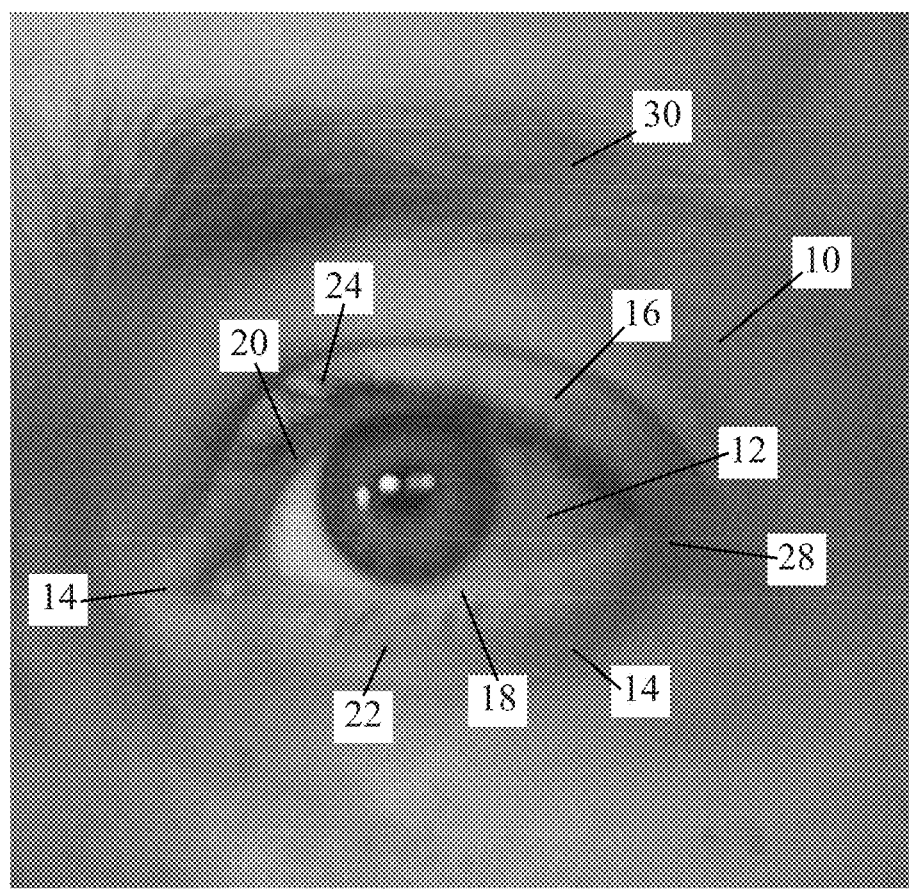
FIG. 1A is a photograph of an eye region of a human face, showing the eye open.
Figure 1B:
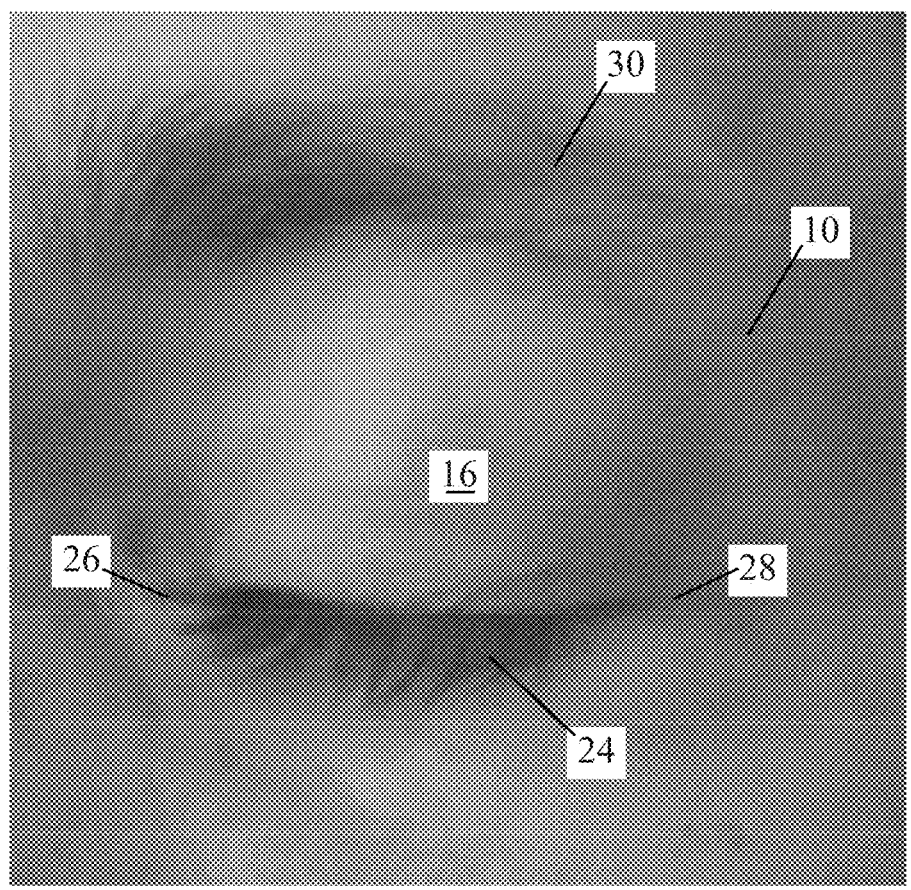
FIG. 1B is a photograph of an eye region of a human face, showing the eye closed.
Figure 1C:
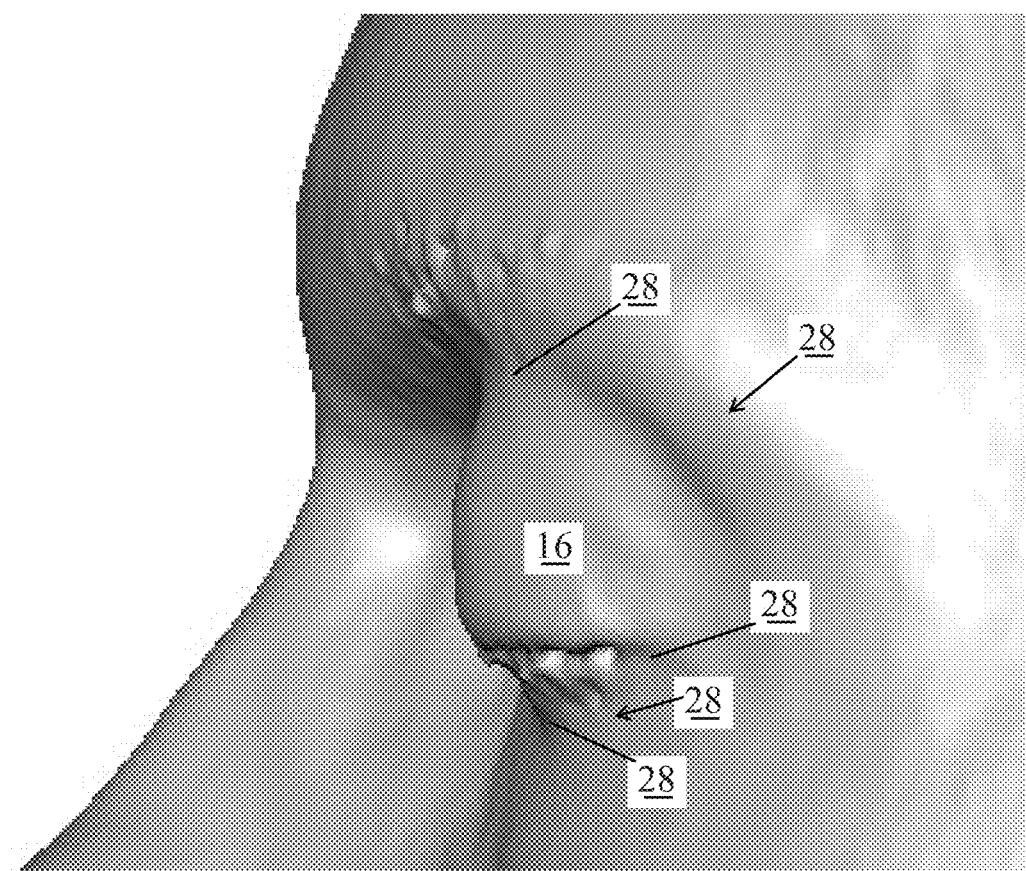
FIG. 1C is a side view of an eye region of a human face, showing the eye closed.

Referring to FIGS. 1A-1C, the eye region 10 of the human face includes an eyeball 12 covered in part, on the bottom by a lower eyelid 14 and on the top by an upper eyelid 16. The lower and upper eyelids 14, 16 each have an inner eyelid liner 18, 20 adjacent the eyeball 12. From the eyelid liners 18, 20 extend lower and upper eyelashes 22, 24. The eye region 10 further includes a medial canthus 26 and a lateral canthus 28. The eyebrow 30 is situated above the upper eyelid 16.

Figure 1D:
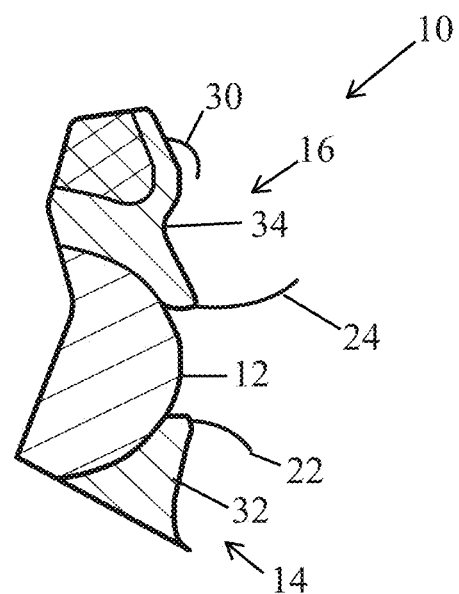
FIG. 1D is a schematic illustration cross section of a side view of an eye region of a human face, showing the eye open.

The bounds of the eyeball 12 can be visually determined externally on the upper and lower eyelids 14, 16. Referring to FIGS. 1A and 1C, the lower bound of the eyeball 12 is disposed at the peak point 32 of an arc of concavity 32 in the lower eyelid 14. Referring to FIGS. 1B and 1C, the upper bound of the eyeball 12 is disposed at the peak point 34 of an arc of concavity 34 in the upper eyelid 16. FIG. 1D is a side view illustrating the concavity in the upper and lower eyelid 14, 16 resulting from the bounds of the eyeball 12.

As used herein, the "height of the eye $H_E$" refers to the maximum distance between the lower eye region bound 66 and the upper eye region bound 68.

Figure 2:
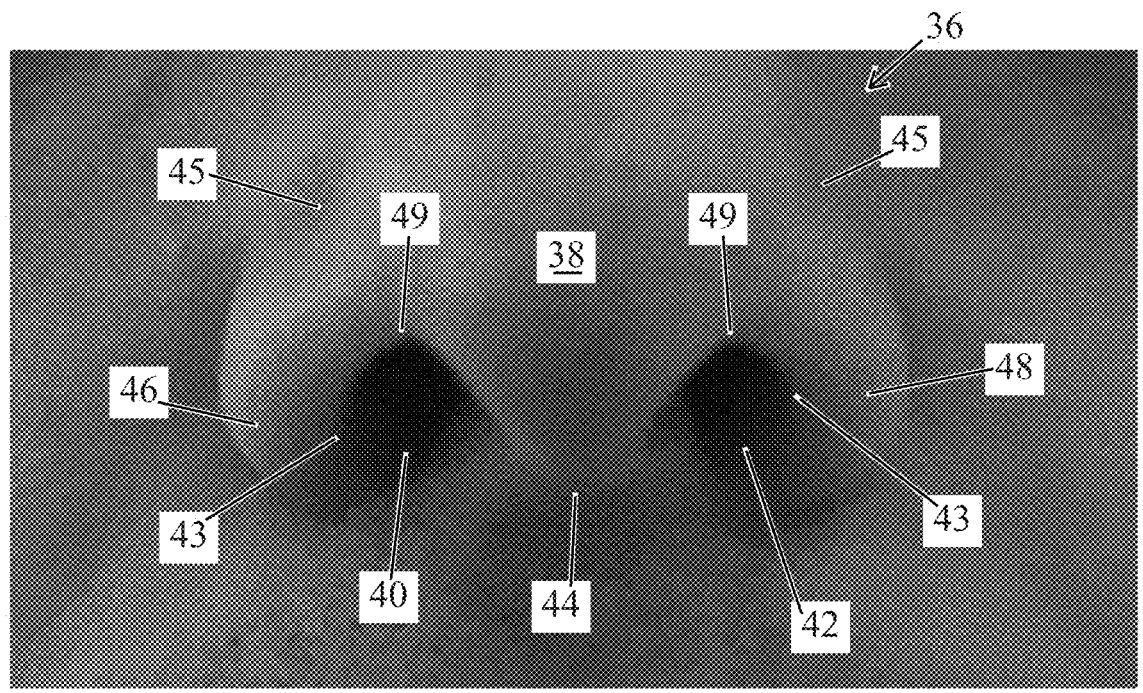
FIG. 2 is a photograph of a nose region of a human face.

Referring to FIG. 2, a nose region 36 can include a central nose tip 38, first and second nostrils 40, 42, and a columella separating the first and second nostrils 40, 42. The first and second nostrils 40, 42 are each bounded by an outer nostril wall 46, 48 and internally by the columella. The columella terminates in a base 44.

Figure 3:
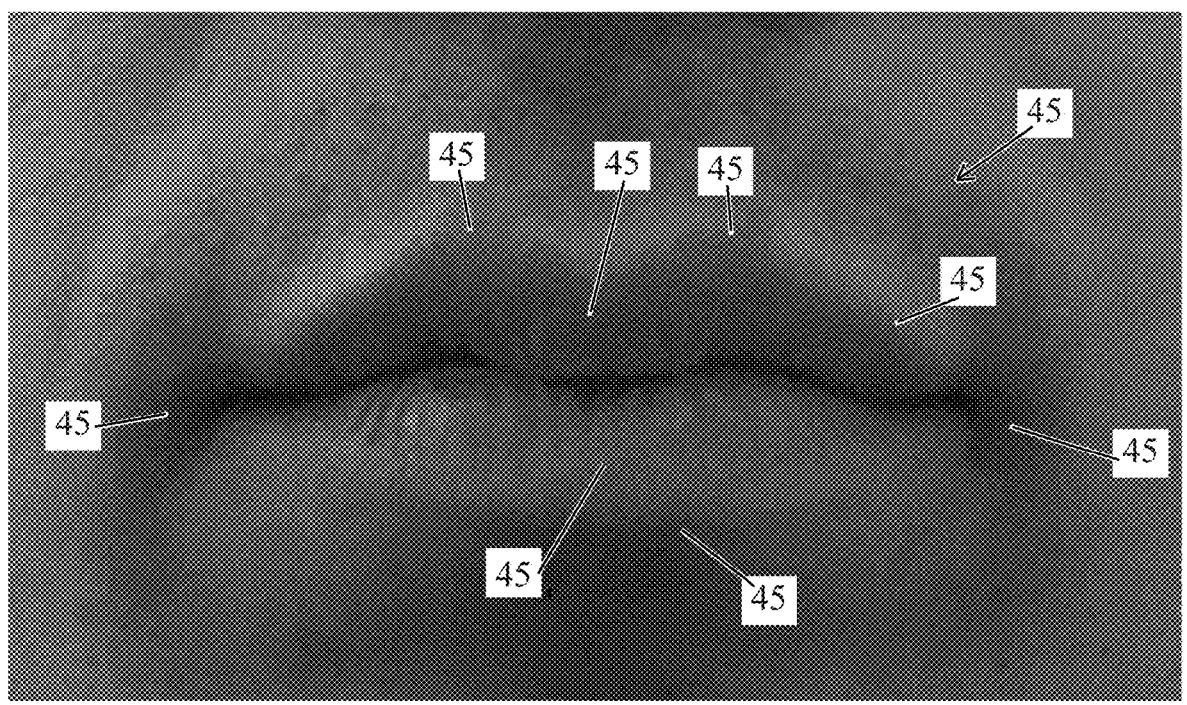
FIG. 3 is a photograph of a mouth region of a human face.

Referring to FIG. 3, a mouth region 50 includes upper and lower lips 52, 54 that are bounded on their outer periphery by the vermillion border 56. The vermillion border has an upper most point 58 in the upper lip 52 and a lower most point 60 in the lower lip 54. The mouth region 50 also includes first and second corners 62, 64 of the mouth.

Figure 14:
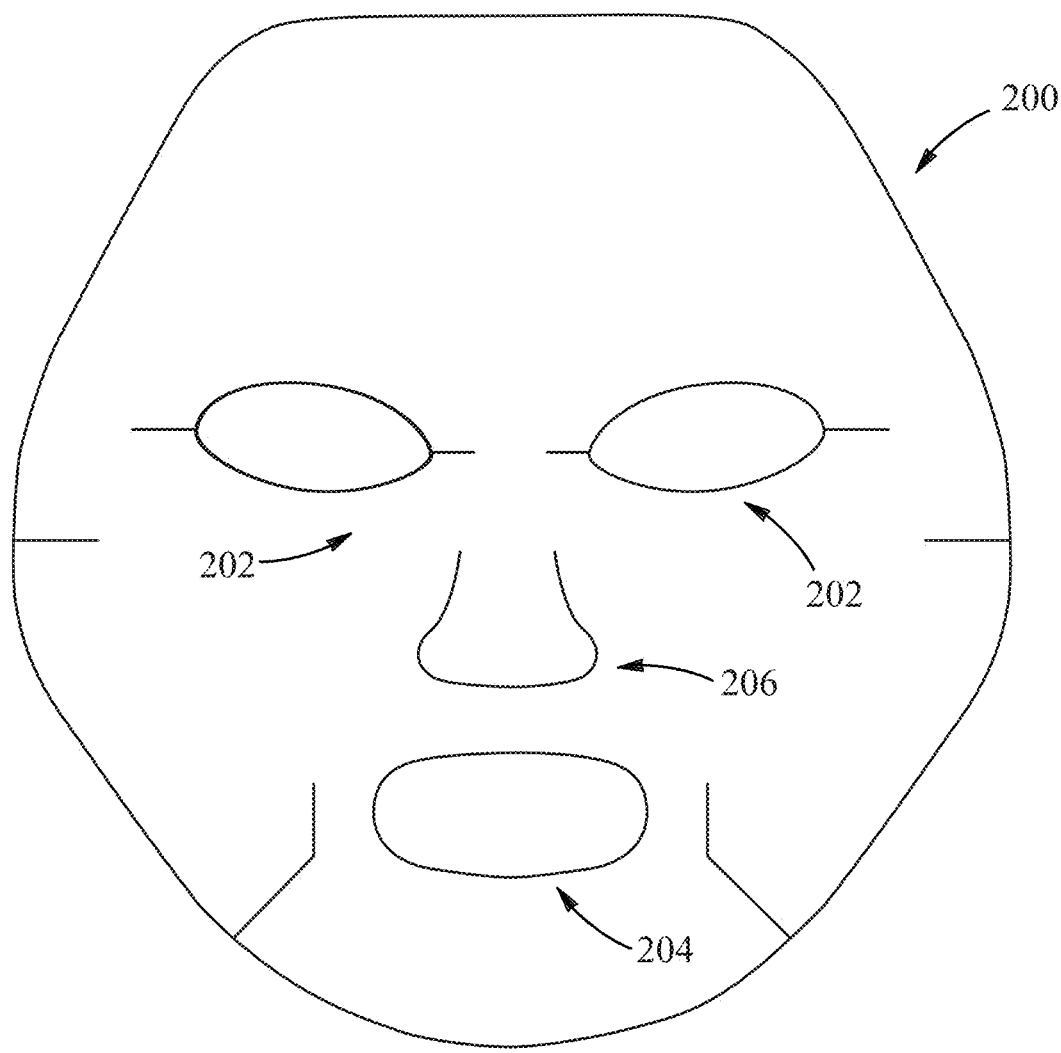
FIG. 14 is a schematic illustration of a conventional, one-size fits all mask having universally sized mouth, nose, and eye openings.

Referring to FIG. 14, conventional face masks 200 are typically flat, two-dimensional masks 200 with one-size fits all eye openings 202 and spacing. Such masks 200 also typically have a one-size fits all opening for the mouth 204 and nostrils 206. When worn, conventional mask 200 do not align well with eyes, and other features of the human face of many users. With respect to the eye region, such conventional, ill-fitting masks 200 can cause discomfort by resting on the eye or covering the eye and/or causing ineffective treatment because the opening overlies the under-eye region to be treated rather than the mask surface having the active, cosmetic, and/or therapeutic agent. Similarly, in the mouth region, ill-fitting masks 200 can either overlap with the lip area or be spaced too far from the lips or nose portions thereof. In the region, ill-fitting masks 200 can interfere or overlap with the nostrils. The methods in accordance with various embodiments of the disclosure advantageously provide custom-fit openings that can allow the mask 200 to align properly, for example in the eye region resulting improved comfort and fit.

Figure 6:
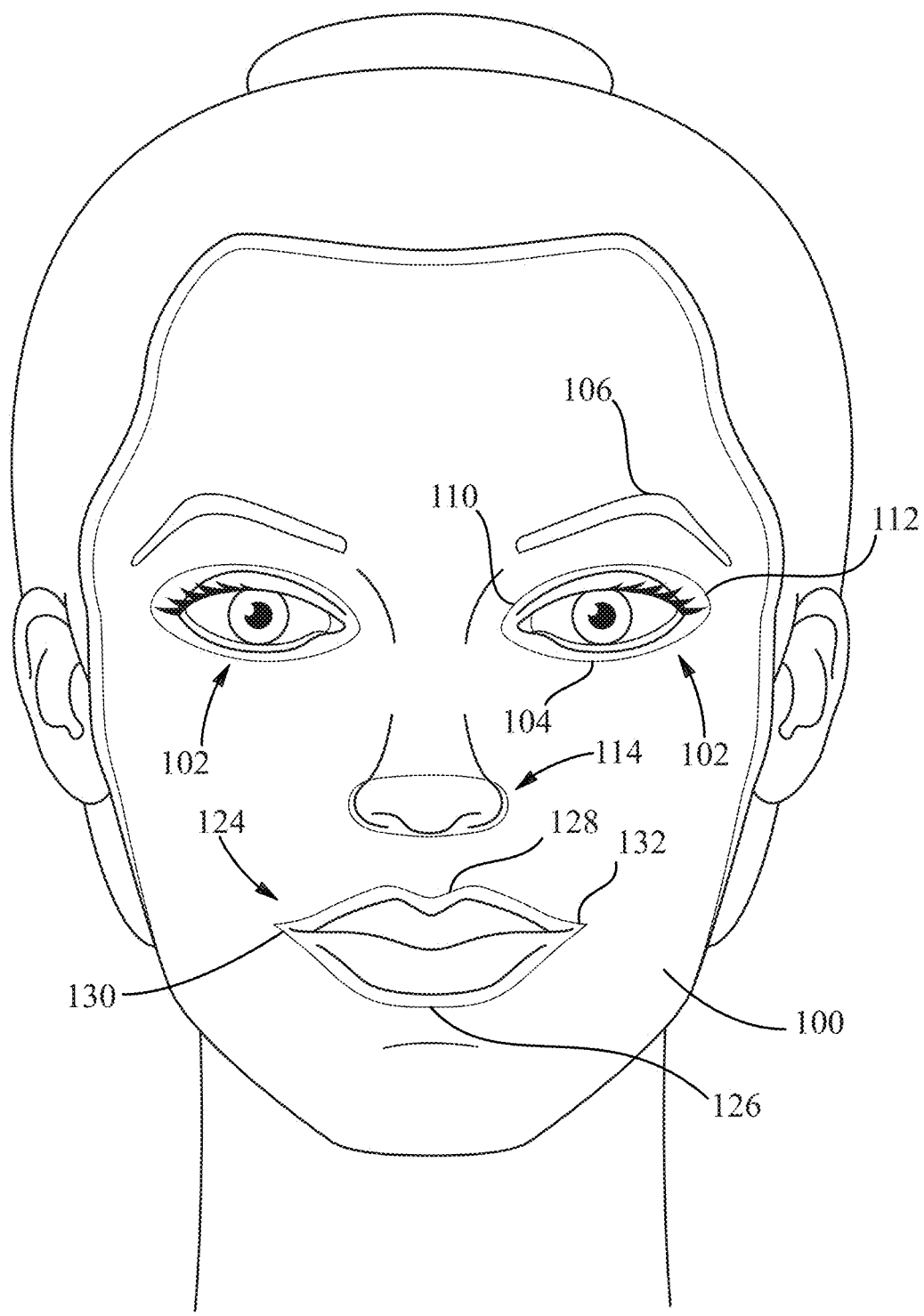
FIG. 6 is a schematic illustration of a face mask fitted to a face in accordance with embodiments of the disclosure.

Referring to FIG. 6, in accordance with embodiments, the methods in accordance with embodiments of the disclosure can provide a mask 100 having an eye opening 102 that can have a lower peripheral edge, first edge 104, that lies close to the inner eyelid liner 18 of the lower eyelid 14 of the user, thereby allowing improved coverage of the under-eye region by the mask 100 portion having an active, cosmetic, and/or therapeutic agent disposed thereon. In accordance with other or further embodiments, the methods in accordance with the disclosure can provide a mask 100 having a pair of eye openings 102 that are spaced such that each opening lies at a desired, close, but non-overlapping position from the medial canthus 26. In accordance with other or further embodiments, the methods in accordance with the disclosure can provide a mask 100 having a nose opening 114 that overlaps partially with the outer nostril walls 46, 48, but does not interfere with the nostrils 40, 42 or cause discomfort when breathing. In accordance with other or further embodiments, the methods in accordance with the disclosure can provide a mask 100 having mouth opening 124 that is spaced close to the vermillion border 56 of both the upper and lower lips 52, 54. In accordance with embodiments of the disclosure, masks and methods of making the same can include any combination of custom-defined openings and/or standard-sized (universal fit) openings. For example, a mask can include a custom-defined mouth opening in accordance with embodiments of the disclosure with standard-sized eye openings. For example, a mask can include custom-defined eye opening in accordance with embodiments of the disclosure with standard-sized nose and/or mouth openings. For example, a mask can include a custom-defined nose opening in accordance with embodiments of the disclosure, with no openings for eyes or mouth. For example, the mask can include custom-defined eye, mouth, and nose openings in accordance with embodiments of the disclosure. Any other such combinations of defined openings are contemplated herein.

The methods and masks 100 in accordance with embodiments of the disclosure provide improved fit and comfort. Improved fit can allow for better contact of the active, cosmetic, and/or therapeutic agents on the mask 100 with desired regions of the face. Desired regions can include one or more of, for example, the under-eye region, the corners of the nose 45 just outboard the outer nostril walls 46, 48, and the skin close to the lips. Improved fit can include masks 100 that cover such desired regions, while not foregoing coverage of other regions, such as above the eye, and/or without interfering with facial features where coverage is to be avoided, such as the eyeball 12, nostril 40, 42, and/or lips 52, 54. Mask 100 in accordance with embodiments of the disclosure can also have improved fit in not only contacting desired regions, but maintaining closer contact without gaps or bubbles in the mask 100 that would disrupt contact with a desired region.

Figure 4:
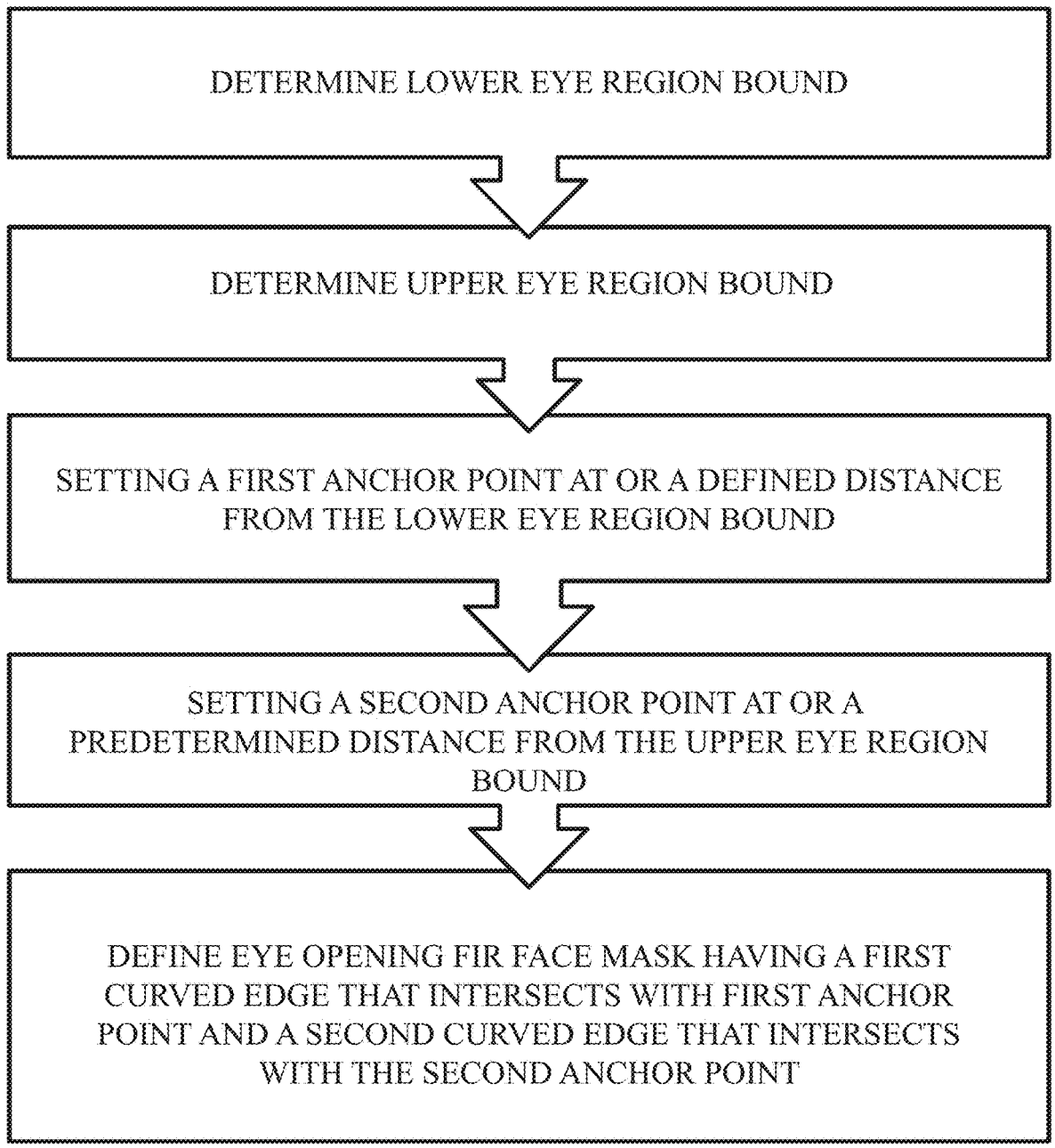
FIG. 4 is a process diagram illustrating a method in accordance with embodiments of the disclosure.

Referring to FIG. 4, in accordance with embodiments of the disclosure, a method of making a mask 100 for a face includes determining a lower eye region bound 66, determining and upper eye region bound 68, setting a first anchor point 0 mm to 10 mm below the lower eye region bound 66 and second anchor point 0 mm to 10 mm above the upper eye region bound 68, and defining at least one eye opening 102 for a face mask 100 having a first edge that intersects with the first anchor point and the second edge that intersects with the second anchor point. As used herein, an anchor point refers to a digital reference point, which is a fixed point in space and selected on a digital representation of the target area.

In accordance with embodiments of the disclosure, a method of making a mask 100 for a face includes determining a lower eye region bound 66; determining an upper eye region bound 68 by locating an upper bound of the eyeball 12; and defining the at least one eye opening 102 such that, when the mask 100 is fitted to the face, the first edge 104 is disposed 0 mm to about 10 mm below the lower eye region bound 66 and the second edge 106 is disposed 0 mm to about 10 mm above the upper eye region bound 68. The method can further include creating the face mask 100 having the at least one eye opening 102. The eye openings may be the same, similar, or distinctly different from each other to accommodate a particular individual's two eyes.

In any of the embodiments herein the upper eye region bound 68 can be one or more of a peak point 34 of an arc of concavity in an upper eyelid 16 of the at least one eye when the eye is closed; a peak point in the fold line in the upper eye lid; a highest point of an upper eyelash 24 when the eye is open; and an edge of the upper eye lid. The highest point of an upper eyelash when the eye is open can be selected in embodiments to be an average highest point among a group or all of the upper eyelashes or alternatively can be the highest point of the longest upper eyelash.

In any of the embodiments herein, the lower eye region bound 66 can be determined by locating one or more of a position of one or more of a lowest extent of one or more lower eyelashes 22 of the at least one eye when the eye is open, a lower bound of the eyeball 12 as determined by a peak point 32 of an arc of concavity in the lower eyelid 14 of the at least one eye when the eye is closed, an edge of the eye ball on the lower side, an edge of the lower eye lid, and a lowest extent of one or more upper eyelashes 24 of the at least one eye when the eye is closed.

In any of the embodiments herein, the creation of the face mask 100 can include exporting data relating to the defined at least one eye opening 102 to a cutting tool to define a cutting path for cutting the eye opening 102 into a mask 100 substrate. Alternatively, the creation of the face mask 100 can include combining the digital data relating to the defined at least one eye opening 102 with digital data associated with the face mask 100 shape to defined in the digital data of the face masks 100 the eye opening 102, which can be exported for direct printing of the masks 100 or molds for making masks 100 having the eye openings 102 formed therein currently with the mask 100 formation. Alternately, the data can be transformed or translated to a cutting path or machine path.

In various embodiments, the curvature of the first and second edges 104, 106 of the eye opening 102 is defined to have a corresponding degree of curvature to the inner lining 18, 20 of the lower and upper eyelid 14, 16.

In various embodiments, the method includes determining a position of the medial canthus 26 and a position of the lateral canthus 28 and setting third and fourth anchor points, respectively, 0 to 10 mm outboard, relative to the eyeball 12, from the medial and lateral canthus 26, 28. In such embodiments, defining the at least one eye opening 102 can include defining a peripheral curve that intersects at a first edge 104 through the first, third, and fourth anchor points, and at a second edge 106 through the second, third, and fourth anchor points. In various embodiments, additional anchor points can be used.

In various embodiments, the method can include or further include determining a position of the medial canthus 26 and a position of the lateral canthus 28 and defining the eye opening 102 such that corners 110, 112 of the eye opening 102 are spaced about 0 mm to about 10 mm outbound, relative to the eyeball 12, from the medial and lateral canthus 26, 28, respectively. Unless otherwise specific, as used herein, "outboard of the medial canthus 26" or "outboard of the lateral canthus 28" refers to positioning outboard from the respective canthus relative to the position of the eyeball 12. That is, the eyeball 12 is considered inboard of the respective canthus.

Figure 5:
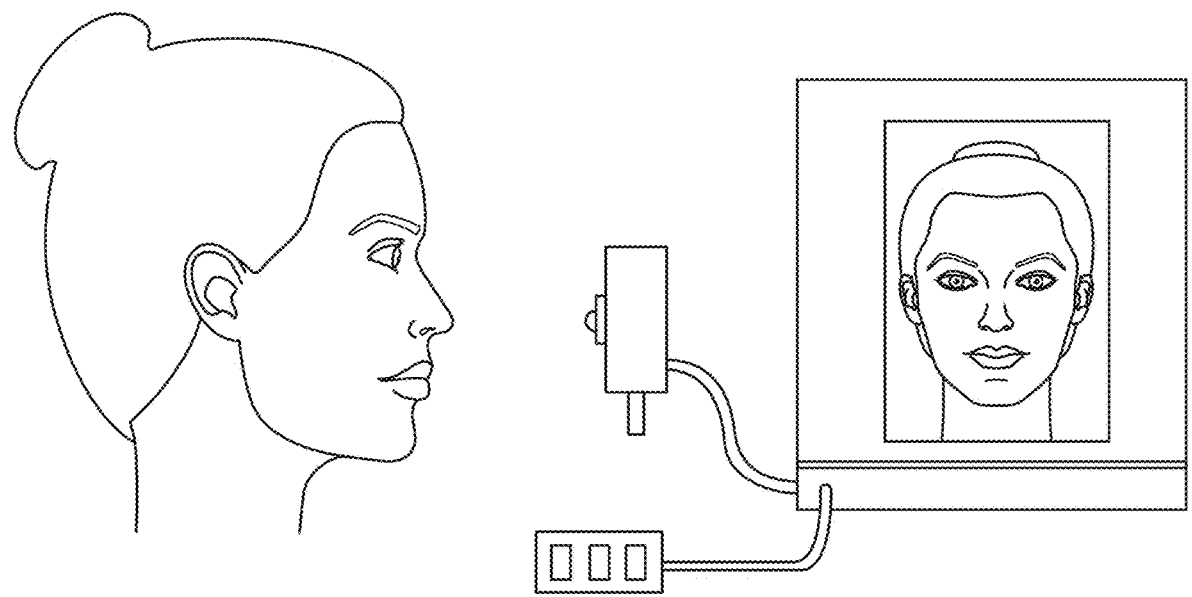
FIG. 5 is a graphical illustration of a step of obtaining a digital image of a human face in accordance with embodiments of the disclosure.

In various embodiments, the method can include obtaining a digital geometric representation of the face of the user. FIG. 5 illustrates one embodiment of obtaining such a digital representation. Any known methods of obtaining a digital representation of an object, such as a face, or converting images to digital geometric representations can be used. In various embodiments, the method can include one or more of displaying, storing, and transmitting of the digital representation or data associated therewith. Any known processes, storage media, and display systems and equipment can be used.

Referring to FIG. 6, in accordance with an embodiment of the disclosure, a mask 100 can include an eye opening 102 defined in accordance with embodiments of the method of the disclosure. As illustrated in FIG. 6, the mask 100 can further include a mouth opening 124 and/or nose opening 114 as discussed in detail below.

Figure 7A:
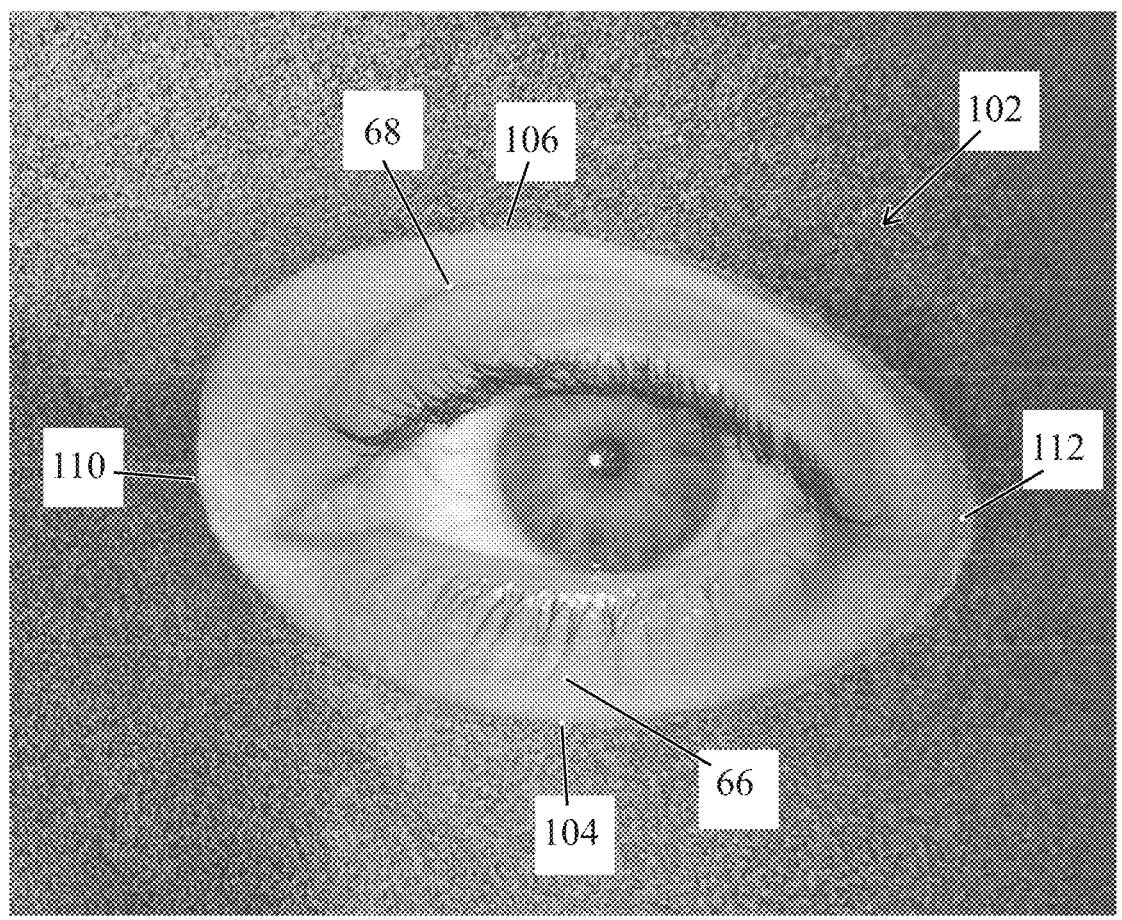
FIG. 7A is a photograph of an eye region of a human face showing a face mask fitted to the eye region having an eye opening in accordance with embodiments of the disclosure, with the eye shown open.

Referring to FIG. 7A, a mask 100 in accordance with various embodiments of the disclosure can have an eye opening 102 having first and second opposed curve edges 104, 106 with the height $H_{EO}$ extending between the edges 104, 106. The first edge 104 can be disposed about 0 mm to about 10 mm below the lower eye region bound 66. The second edge 106 can be disposed about 0 mm to about 10 mm above the upper eye region bound 68. The height $H_{EO}$ of the eye opening 102 can be defined by the maximum distance between the first edge 104 and the second edge 106. In various embodiments, the mask 100 can have an eye opening 102 height $H_{EO}$ at least equal to the height of the eye $H_E$.

A mask 100 in accordance with embodiments of the disclosure can have a first edge 104 of an eye opening 102 that is disposed about 0 mm to about 10 mm below a lower eye region bound 66 when the mask 100 is worn. In accordance with various embodiments, the eye opening 102 can include second edge 106 that is disposed about 0 mm to about 10 mm above the upper eye region 10 bound 68 when the mask 100 is worn.

In various embodiments, the mask 100 can include or further include an eye opening 102 having first and second corners (also referred to as side edges) 110, 112 that are spaced from the medial and lateral canthus 26, 28, respectively, about 0 to about 10 mm outboard, from the medial and lateral canthus 26, 28. The spacing of the first and second corners 110, 112 from the medial and lateral canthus 26, 28, respectively, can be the same or different.

In any of the embodiments herein, the mask 100 or method of making a mask 100 can include defining the mask 100 to have first and second eye openings 102 corresponding to both eyes of the user.

In various embodiments, the mask 100 or method of making a mask 100 can include defining a registration feature in the mask 100 to aid in aligning the mask 100 when worn. For example, in embodiments, the registration feature can be a portion of the mask 100 covering one or more of the nose or portion thereof, the chin or portion thereof, and a jaw section. Inclusion of coverage of such portions of the mask 100 can aid the users in aligning the mask 100 upon application such that the openings of the mask 100 properly align with the target region.

In accordance with embodiments, the method can further include determining the relative spacing between the eyes of the users and defining a mask to have a spacing that is within 0 mm to 10 mm of the spacing between the eyes of the user. The spacing between the eyes of a user can be defined as the spacing between the medial canthus 26 of each eye and the spacing between the eye openings of the mask can be defined between the first corners of each eye opening. In embodiments, the method can further include determining the relative spacing between one or more features to which an opening is to be defined. For example, where a mask 100 is being created to have an eye opening and a mouth opening, a spacing between a feature of the mouth and a feature of the eye can be determined and the mask can be defined to have a spacing that is about 0 mm to about 10 mm of this spacing, with the mask spacing between defined between features or bounds of the opening disposed adjacent the selected features of the eye and mouth. Such determination of relative spacing of facial features and associated openings can be done with any openings and target areas. For example, relative spacing between nostrils or the base of the columella and the upper lip can be used to define spacing between the upper bound of the mouth opening and lower bound of the nose opening. In some embodiments the pupillary distance (PD) or interpupillary distance (IPD) may be used to determine relative spacing between the eyes.

In any of the embodiments disclosed herein, the mask 100 can be a two-dimensional mask or a three-dimensional mask. In accordance with embodiments, a two-dimensional mask can be a substrate mask, nonwoven mask, woven mask, knit mask, paper mask, cotton mask, any other type of woven, nonwoven, gel, hydrogel type of mask made of natural or synthetic fibers, composites, gel, hydrogels, films, apertured films or any other such mask making materials as is known in the art. In any of the embodiments disclosed herein, the three-dimensional mask can be a self-supporting mask. As used herein, the term "self-supporting" means that an element of or the applicator in its entirety retains a substantial portion of a defined three-dimensional shape without the aid of external support structures when resting on a horizontal surface in air. In any embodiment, the mask may be a semi-three dimensional mask where cuts, folds, or seams are used in a flat substrate material to create a less flat or more three-dimensional mask. In any of the embodiments disclosed herein, the mask can be a single-dose applicator or for single use having a single dose of the active, cosmetic, and/or therapeutic. As used herein, the term single-dose means an applicator comprising sufficient active agents to afford a user only a single application of the active agent via the applicator. In any of the embodiments disclosed herein, the mask can be for multiple use. For example, active, cosmetic, and/or therapeutic agents can be applied and successively reapplied for multi-use. In any of the embodiments disclosed herein, the mask can be disposable. As used herein, the term disposable refers to applicators intended to be discarded after use rather than durable, or semi-durable implements intended for multiple users either with or without the reapplication of an active agent. In any embodiment, the mask can be a durable item suitable for washing by hand or in a dishwasher or clothing washing machine.

In various embodiments, the lower eye region bound 66 can be defined at one or more of the lowest one of the lowest extent of one or more lower eyelashes 22 of the at least one eye when the eye is open, a lower bound of the eyeball 12 as determined by a peak point 32 of an arc of concavity in the lower eyelid 14 of the at least one eye when the eye is closed, and a lowest extent of one or more upper eyelashes 24 of the at least one eye when the eye is closed. For example, in embodiments, the peak point 32 of an arc of concavity in the lower eyelid 14 can be determined manually by rotating a three-dimensional image of the face or eye region thereof and digitally altering the angle of the light to estimate the location of the peak point 32 of the arc of concavity. In embodiments, for example, the peak point 32 of the arc of concavity in the lower eyelid 14 can be determined by taking cross-sections in a three-dimensional image of the face or eye region, perpendicular to the direction of the curvature that is vertically from the forehead to chin and observing the lowest point in the cross-section. The cross-sections can be taken at one or more reference points in the eye region to define points which are then connected to form the arc of concavity defining the eye boundary. In yet other embodiments, an algorithm, such as a machine learning algorithm, neural net, or deep learning algorithm can be used to teach a software tool to identify the peak point 32 of an arc of concavity on a digital representation of the face or at least the eye region thereof.

For any of the reference points or anchor points disclosed these may be identified manually or through a machine learning algorithm, image analysis, or other approach, for example facial landmark detection such as Dlib (available from github). Reference points or anchor points may be determined in part through an app and or by a user. Pixels in a 2D image or 3D information may be used to select the anchor points through edge finding algorithms, feature extraction, using texture, color, RBG or grayscale values, shadows, or other features from a 2D image or 3D surface. In various embodiments, the lower eye region bound 66 is the lowest one of the lowest extent of one or more lower eyelashes 22 of the at least one eye when the eye is open. In some embodiments, the lower eye region 66 bound is the lower bound of the eyeball 12 as determined by a peak point 32 of an arc of concavity in the lower eyelid 14 of the at least one eye when the eye is closed. In some embodiments, the lower eye bound is the upper most one of the lowest extent of one or more lower eyelashes 22 of the at least one eye when the eye is open.

In various embodiments, the lower eye region bound 66 is the lowest extent of one or more lower eyelashes 22 of the at least one eye when the eye is open. For example, the lower eye region bound 66 can be the lowest extent of the longest one of the lower eyelashes 22 of the at least one eye. Alternatively, the lower eye region bound 66 can be defined at an average of the lowest extents of each of the lower eyelashes 22.

Figure 7B:
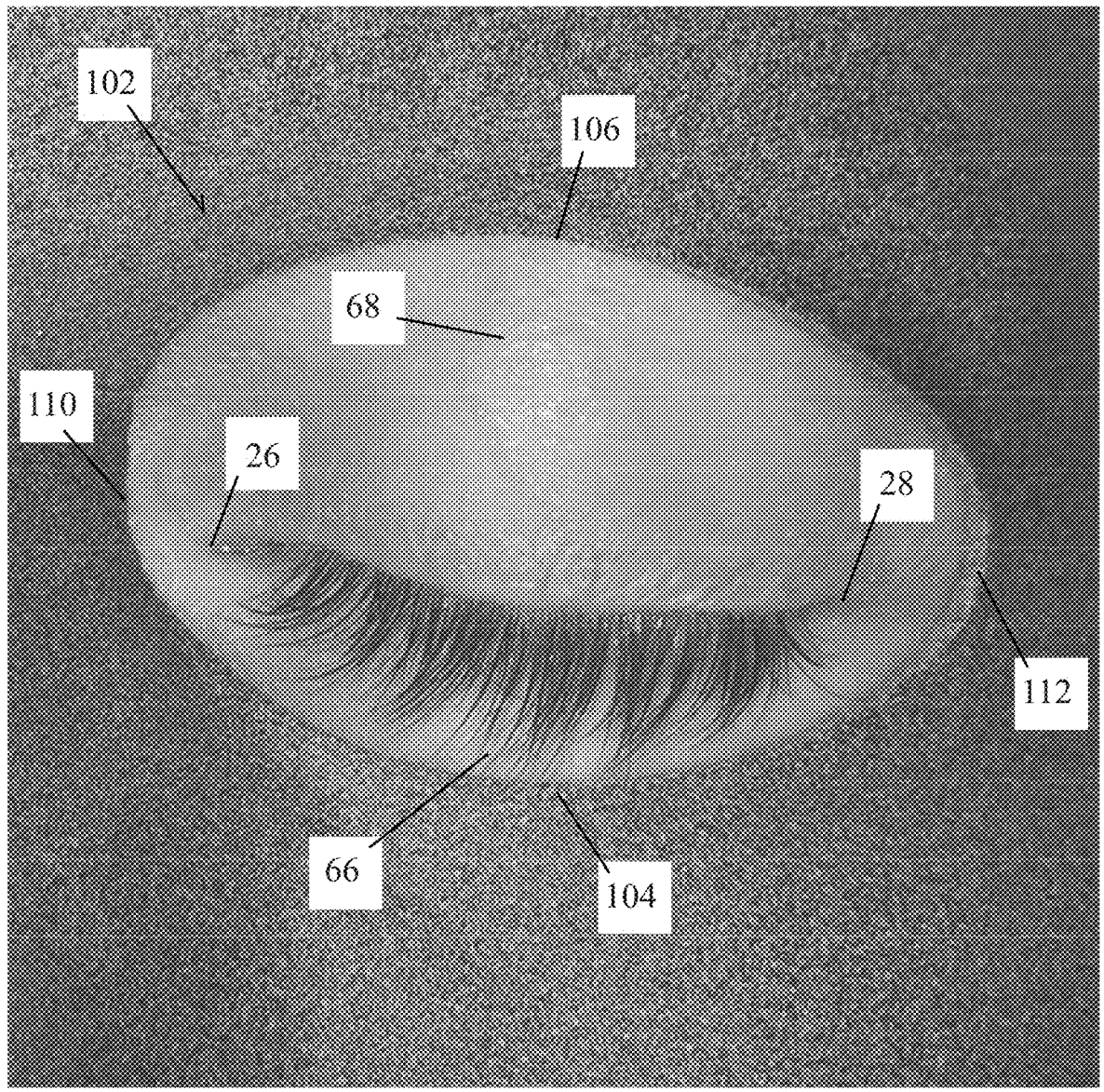
FIG. 7B is a photograph of the eye region and face mask of FIG. 7A, showing the eye closed.

FIGS. 7A and 7B illustrate an embodiment of the mask 100 and method of the disclosure in which the lower eye region bound 66 is selected to be the peak point 32 of an arc of concavity in the lower eyelid 14 of the at least one eye when the eye is closed. FIG. 8 illustrates an embodiment of the mask 100 and method of the disclosure in which the lower eye region bound 66 is selected to be the lowest extent of one or more lower eyelashes 22 when the eye is open.

In various embodiments, the eye opening 102 of the mask 100 has or is defined to have a first edge 104 that is arranged to contact or have a defined spacing from the lower eye region bound 66 when the mask 100 is worn. The first edge 104 of the eye opening 102 can be positioned from about 0 mm to about 10 mm below the lower eye region bound 66. For example, the first edge 104 of the eye opening 102 can about 0 mm to about 10 mm, about 1 mm to about 4 mm, about 0 mm to about 5 mm, about 2 mm to about 6 mm, about 1 mm to about 8 mm, and about 5 mm to about 10 mm. In various embodiments, the first edge of the eye opening 102 can be about 0, 0.5, 1, 1.5, 2, 2.5, 3, 3.5, 4, 4.5, 5, 5.5, 6, 6.5, 7, 7.5, 8, 8.5, 9, 9.5, or 10 mm below the lower eye region bound 66. In various embodiments, the lowest point of the first edge 104 of the eye opening 102, farthest from the lower eye region bound 66 can be used as the reference point for measuring the distance between the lower eye region bound 66 and the first edge 104 of the eye opening 102.

Positioning of the first edge 104 of the eye opening 102 about 0 to 10 mm from the lower eye region bound 66 can advantageously provide an eye opening 102 that has tight fit to the eye, allowing maximum coverage of the under-eye region, without causing discomfort by interfering with the lower eyelashes 22 or overlapping too closely with the edge of the lower eyelid 14.

In embodiments, the upper eye region bound 68 can be determined by locating an upper bound of the eyeball 12 as determined by a peak point 34 of an arc of concavity in an upper eyelid of the at least one eye when the eye is closed. The mask 100 can have an eye opening 102 that is positioned when worn such that the second edge 106 is at or above the upper eye region 68. Eye openings 102 positioned at or above the peak point 34 of an arc of concavity in the upper eyelid have been found to have improved comfort to the user, as the mask 100 does not rest on the upper eyelid 16 in such a way to interfere with movement of the eyelid or eyeball 12.

In various embodiments, the second edge 106 can also or alternatively be spaced to be at or above the highest extent of the upper eyelashes 24 when the eye is open. In various embodiments, the highest extent of the upper eyelashes 24 can be the highest extent of the longest one of the upper eyelashes 24 of the at least one eye. Alternatively, the highest extent of the upper eyelashes 24 can be the average of the highest extents of each of the upper eyelashes 24.

The second edge 106 of the eye opening 102, can be positioned from about 0 mm to about 10 mm above the upper eye region 10 bound. For example, the second edge of the eye opening 102 can about 0 mm to about 10 mm, about 1 mm to about 4 mm, about 0 mm to about 5 mm, about 2 mm to about 6 mm, about 1 mm to about 8 mm, and about 5 mm to about 10 mm, above the upper eye region 10 bound. In various embodiments, the first edge of the eye opening 102 can be about 0, 0.5, 1, 1.5, 2, 2.5, 3, 3.5, 4, 4.5, 5, 5.5, 6, 6.5, 7, 7.5, 8, 8.5, 9, 9.5, or 10 mm above the upper eye region 10 bound. In various embodiments, the highest point of the second edge of the eye opening 102, farthest from the upper eye region 10 bound can be used as the reference point for measuring the distance between the eye region 10 bound and the second edge of the eye opening 102.

Figure 8A:
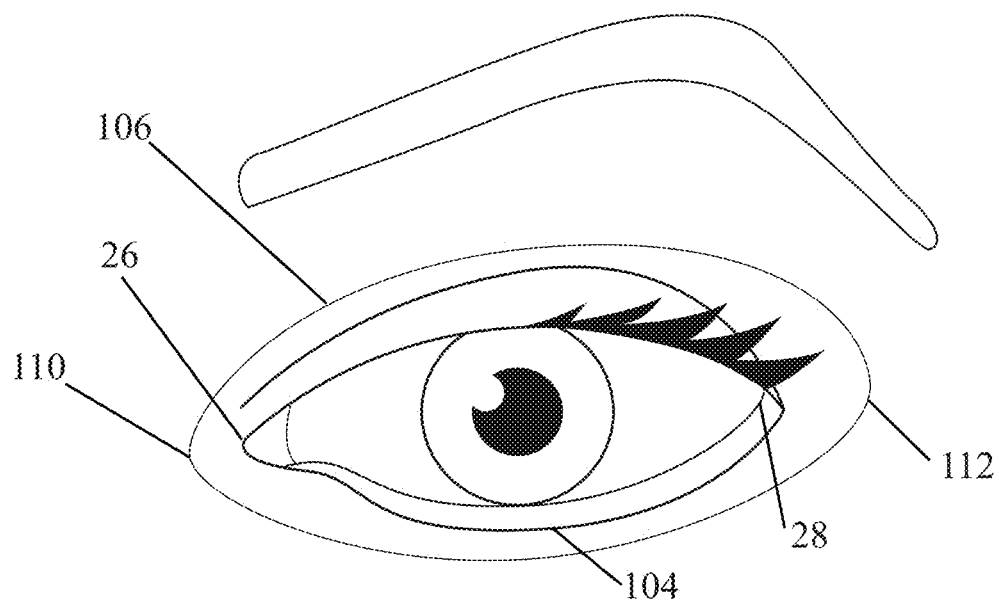
FIG. 8A is a front view of an eye opening of a mask fitted to an eye region in accordance with embodiments of the disclosure.
Figure 8B:
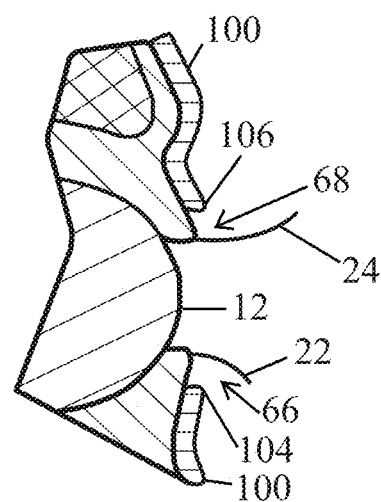
FIG. 8B is a side view cross section of the eye opening of the mask of FIG. 8A.
Figure 9A:
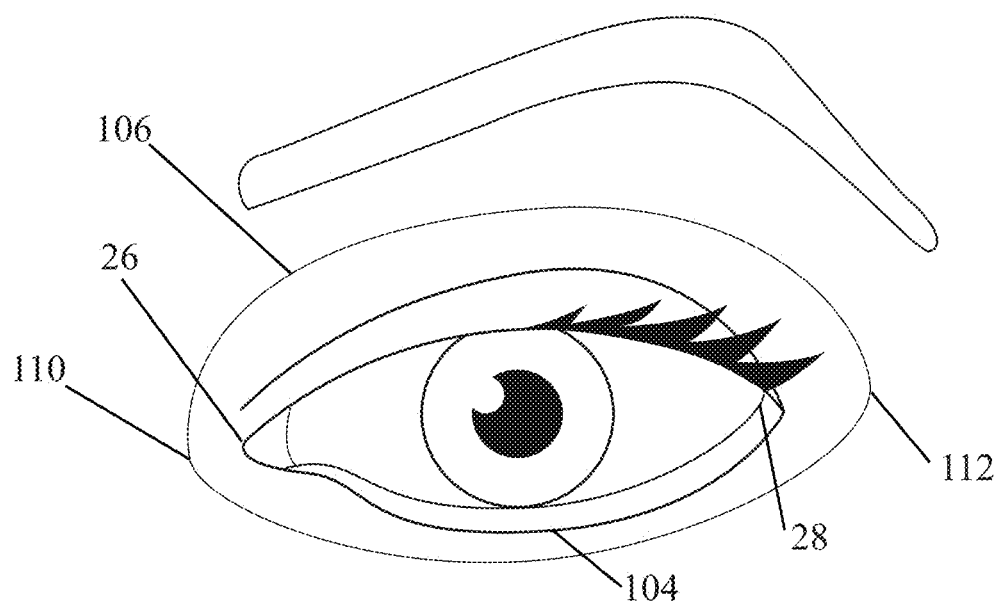
FIG. 9A is a front view of an eye opening of a mask fitted to an eye region in accordance with embodiments of the disclosure.
Figure 9B:
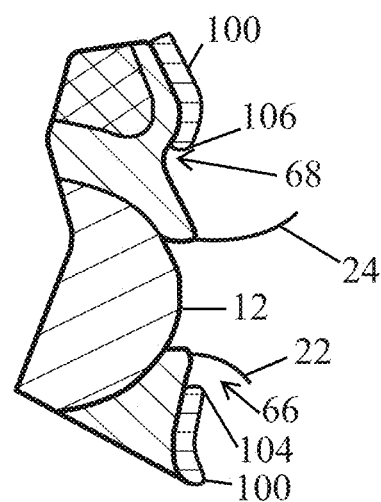
FIG. 9B is a side view cross section of the eye opening of the mask of FIG. 9A.
Figure 10A:
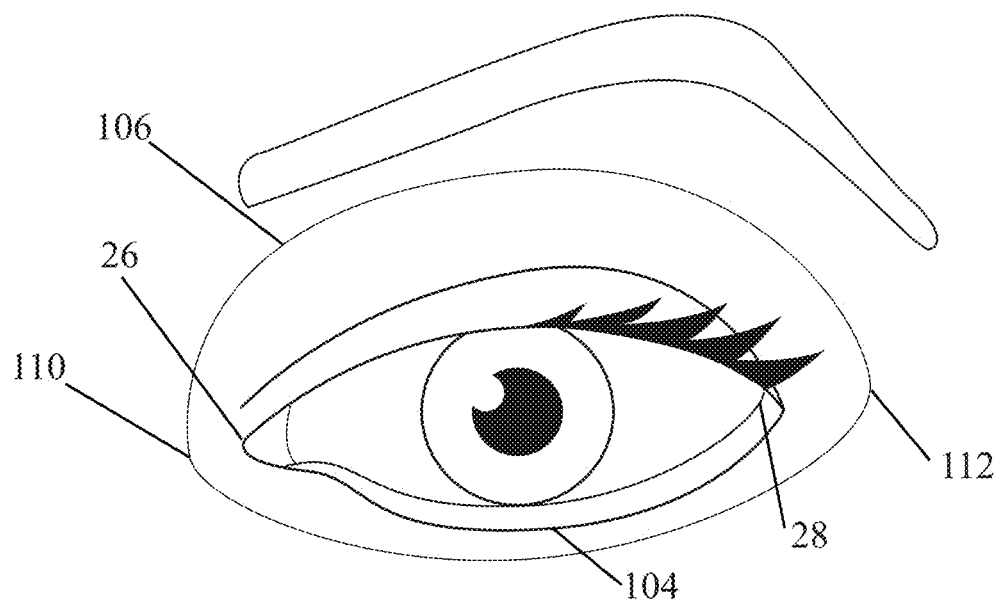
FIG. 10A is a front view of an eye opening of a mask fitted to an eye region in accordance with embodiments of the disclosure.
Figure 10B:
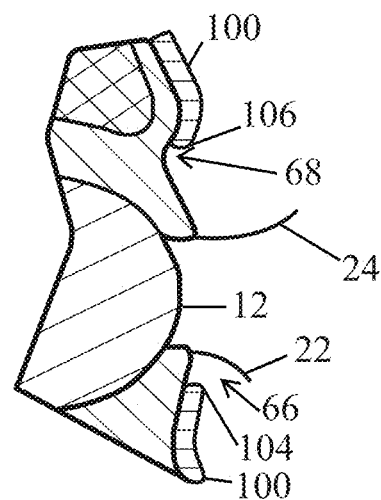
FIG. 10B is a side view cross section of the eye opening of the mask of FIG. 10A.
Figure 11A:
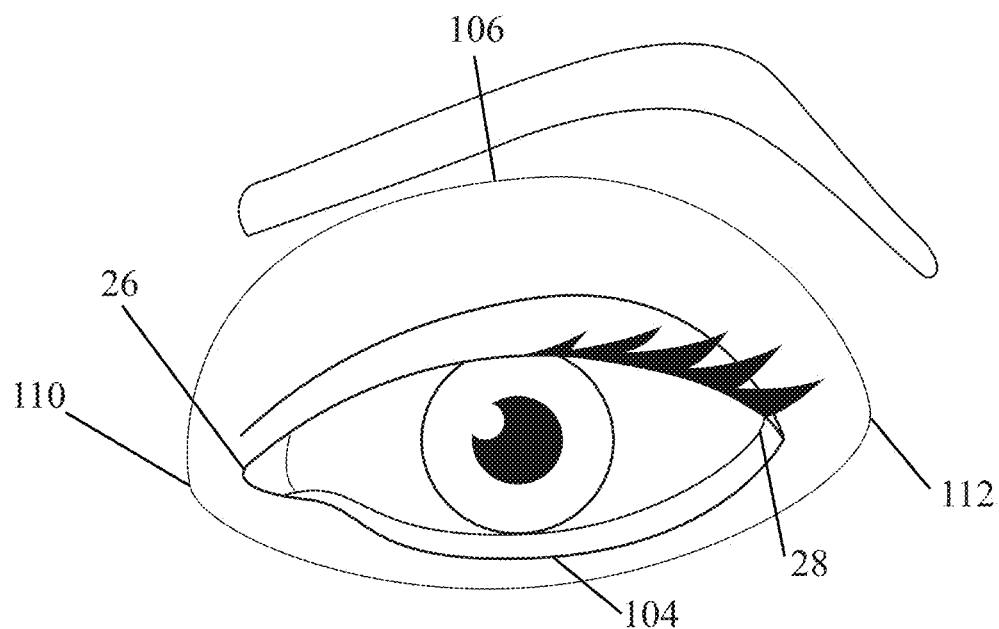
FIG. 11A is a front view of an eye opening of a mask fitted to an eye region in accordance with embodiments of the disclosure.
Figure 11B:
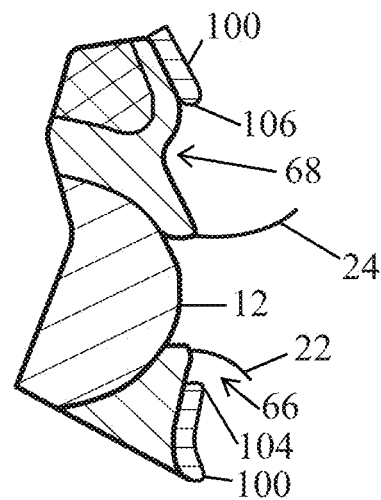
FIG. 11B is a side view cross section of the eye opening of the mask of FIG. 11A.

FIGS. 7A and 7B illustrate an embodiment in which the second edge 106 is disposed within 0-10 mm the peak point 34 of an arch of concavity in the upper eyelid 16. FIGS. 8A and 8B illustrate an embodiment in which the second edge 106 is spaced a distance above the peak point 34 of an arc of concavity in the upper eyelid 16 and at the highest extent of the upper eyelashes 24. FIGS. 9A and 9B and 10A and 10B illustrate an embodiment in which the second edge 106 is spaced from the upper eye region bound 68 a distance of about 2 to about 4 mm FIGS. 11A and 11B illustrate an embodiment in which the second edge 106 is disposed near an edge of the eye socket.

In accordance with embodiments of the disclosure, the method can include obtaining one or more digital geometric representations of at least one eye region 10 of the user's faces. The digital geometric representations can include variations in which the user's eye is open and the user's eye is closed. The digital geometric representation can include images or scans representing front profiles and/or side profiles of the user. In various embodiments, the digital geometric representation can be of the entire user's face or of the entire eye region 10, including both eyes or any portion of the user's face including at least one eye region 10.

The digital geometric representation can be obtained, for example, by any one or more of 3D scanners, 2D scanners, cameras, smartphone camera, digital applications for tablets and phones, and other known equipment for obtaining digital geometric data. An Artec Spider, available from Artec Group Palo Alto, CA is an example of a suitable 3D scanner. An example mobile application for a cellular phone or table is 123D Catch from Autodesk or Capture: 3D Scan Anything" by developer, Standard Cyborg or Bellus3D FaceApp by Bellus3D Inc. or the TrueDepth camera system form Apple.

The digital geometric representation of the human face or portion thereof can be used as a whole or partitioned with only a portion of the total representation being used. Furthermore, portions of the geometry derived from the scan or other imaging technique can be removed or edited from the digital geometric representation. The digital geometric representation data may be used without alteration, or the geometry of the representation may be altered. For example, digital processing may be used to alter the digital data. For example, the digital data can be altered to be provided as a mesh to allow for measurement of various features on the digital data. For example, a two dimensional set of data from an image or scan can be altered to provide a three-dimension representation of the two-dimensional data.

In any of the embodiments of the disclosure, any one or more of the various digital processing equipment, digital geometric representations, graphics programs, and graphical displays may be stored in a tangible computer readable memory or medium and/or shared or cloud-based medium, and execute one or more processors to perform the functions described herein. For example, in embodiments, the digital geometric representation can be obtained by a user using a smartphone camera and/or mobile application and subsequently uploaded to a manufacturer's shared memory or medium for manufacturing of the mask 100. In other embodiments, digital geometric representations can be obtained with scanners or other imaging devices located at the point of sale of the mask 100. The data from the digital geometric representations can be stored locally or on a shared medium.

In various embodiments, the lower and upper eye region bounds 66, 68 are defined using the digital geometric representation. Various graphics programs can be used for obtaining measurements and manipulations of the data of digital geometric representation. For example, Blender, by Blender Foundation can be used to view, manipulate, and/or modify the digital geometric representation data. In various embodiments, the digital geometric representations can be used to define anchor points corresponding to the lower and upper eye region bounds 66, 68. The methods in accordance with embodiments of the disclosure include defining at least two anchor points for an eye opening 102. In some embodiments, the method can include defining more than two anchor points. For example, in embodiments, the method can include defining four anchor points corresponding to the upper eye region bound 68, lower eye region bound 66, medial canthus 26, and lateral canthus 28. Any suitable number of anchor points can be defined.

In various embodiments, the anchor points are used to define the peripheral edges of the eye opening 102. As described herein, the anchor points can be set at or offset a distance from the respective target feature of the eye. For example, an anchor point can be about 0 mm to about 10 mm below an anchor point corresponding to the lower eye region bound 66. For example, an anchor point can be about 0 mm to about 10 mm above an anchor point corresponding to the upper eye region bound 68. In any of the embodiments, an anchor point can be off-set about 0 mm to about 10 mm from the respective target feature of the eye region.

Once the at least two anchor points are defined, the method can include fitting one or more curves to the anchor points. For example, a Bezier curve can be used to fit curves corresponding to the peripheral edges of the eye opening 102 to the at least two anchor points. In any embodiments disclosed herein one or more of the following can be used to connect or touch anchor points for defining an opening: Bezier curves, linear segments, parabolas, concave curves, regular or irregular curves, and polygons. In various embodiments, the connector, which defines the edge of the opening can be curved or can have any of the shapes described above. In various embodiments, the connector can mimic, follow, or parallel in whole or in part curvatures and pathways of the underlying physiology of a feature in the target region. For example, the connector can mimic, follow, or parallel the curvature of an eye brow, and eye fold, or an eye shape. Such mimicking, following, or paralleling can aid in conforming the opening to a particular user's face functionally and can provide a more aesthetically pleasing wear experience. In other embodiments, a curve can be defined on the digital geometric data from the curvature of the lining of the upper and lower eyelid and digitally shifted to intersect with the anchor point. Other methods of fitting curves to points can be used as is known in the art. In embodiments using a Bezier curve, a curve can be digitally overlaid over the digital representation in the eye region 10 and handles of anchor points can be adjusted in succession until the curve follows the points of lowest curvature tracing the underlying eyeball 12 and intersect the anchor points.

Once the curve of the eye opening 102 is defined digitally, the data can be exported in any suitable file format to be used in creating the mask 100. For example, the curve can be converted to a mesh using a series of segments that allows for export to cutting tools or other digital tool for printing the mask 100 or defining a mold for making the mask 100. For example, the data of the curve can be converted to mesh and exported as a DXF file. When converting the curve defining the eye opening 102 into a mesh, about 30 to about 100 segments can be used. For example, a mesh can be generated using about 30 to about 100 segments, about 50 to about 100 segments, about 30 to about 60 segments, about 40 to about 80 segments, or about 70 to about 90 segments. Other suitable numbers of segments include about 30, 35, 40, 45, 50, 55, 60, 65, 70, 75, 80, 85, 90, 95, and 100 segments. In some embodiments, the digital mesh of the curve defining the eye opening 102 is exported to a digital cutting tool and used as a cutting path for cutting an eye opening 102 in a mask 100 material.

In other embodiments, the mesh of the curve can be used in generated a digital geometric representation of the mask 100 to be created with eye openings 102 rather than have the eye openings 102 subsequently cut out after mask 100 formation, formation may be accomplished by any method, including but not limited to, thermoforming, hydroforming, hydraulic forming, and vacuum forming. In embodiments, the eye openings can be cut by any method, including but not limited to: laser cutting, water jet cutting, hand cutting, die cutting, hot air cutting—as described in United States Patent Application Publication No. 2017/0354805, incorporated herein by reference. For example, digital printing devices of methods of creating mask 100 materials using various technologies, such as SLS, SLA, FDM, CLIP, and other additive manufacturing technologies that are known in the art could be used. The mesh of the curve of the defined eye opening 102 can be incorporated into a mesh of the mask 100 to digitally eliminate mask 100 material in the eye opening 102, thereby defining the mask 100 having preformed eye openings 102. In an embodiment, the mesh of the curve of the eye opening 102 can be digitally placed over the eye of a face mesh defining the mask 100 region and extruded in the negative Z direction to intersect and pass through the face mesh. The intersection area of the face mesh inbound of the curve is selectively removed to define the opening. Digital removal of a portion of a mesh can be achieved, for example, using a Boolean difference. The data associated with the mask 100 having the digitally removed region to define the custom eye openings 102 can then be exported to suitable printing or manufacturing equipment for formation of the mask 100 itself.

In accordance with various embodiments, methods of making a mask 100 can include or further include defining one or more of a nose opening 114 and a mouth opening 124 in the mask 100.

Figure 12:
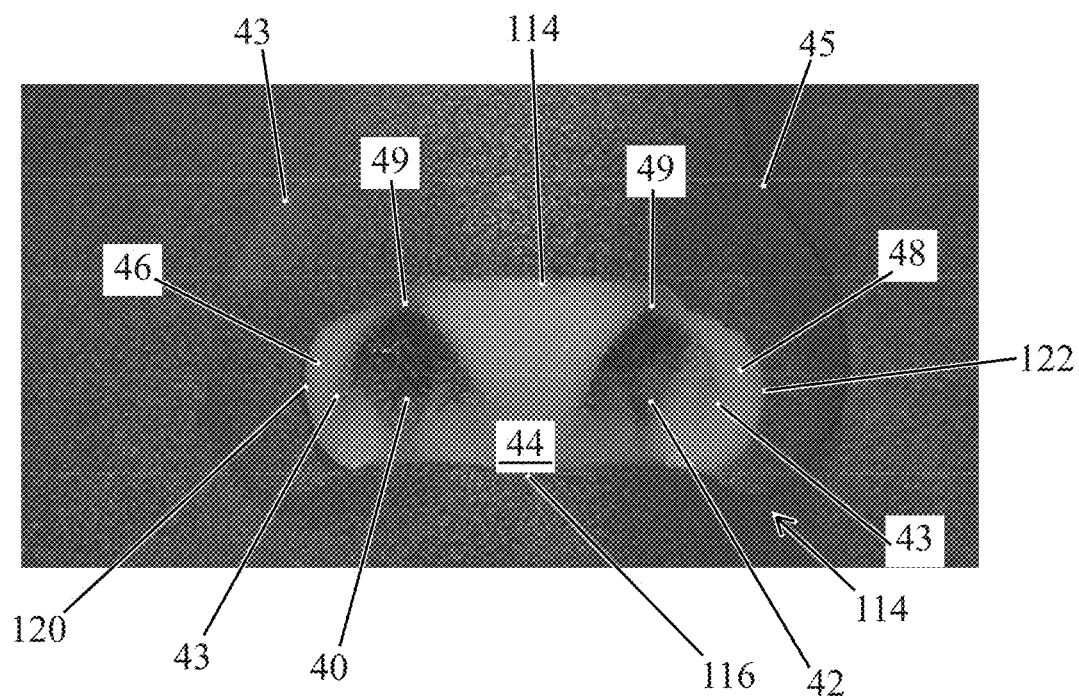
FIG. 12 is a photograph of a nose region of a human face, showing a face mask fitted to the nose region having a nose opening in accordance with embodiments of the disclosure.

In accordance with various embodiments, the mask 100 can include or further include a nose opening 114. The nose opening 114 can be defined, for example to allow the user to breath comfortably while the mask 100 is worn, while maintaining close coverage of the nose region 36 and particular the outer corners of the nose 45. Referring to FIG. 12, the nose opening 114 can have a height $H_{NO}$ extending between first and second edges 116, 118, and a width $W_{NO}$ extending between third and fourth edges 120, 122. In various embodiments, the mask 100 can have a nose opening 114 such that the third and fourth edges 116, 118 at least partially overlap with the outer nostril wall 46, 48. For example, the third and fourth edges 116, 118 can be disposed on the outer nostril wall 46, 48, spaced about 0 mm to about 10 mm from the outermost edge 43 of the respective nostril 40, 42. For example, the spacing can be about 0 mm to about 10 mm, about 0 mm to about 5 mm, about 2 mm to about 6 mm, about 1 mm to about 5 mm, about 3 mm to about 5 mm Other suitable spacings can include, for example, about 0, 1, 1.5, 2, 2.5, 3, 3.5, 4, 4.5, 5, 5.5, 6, 6.5, 7, 7.5, 8, 8.5, 9, 9.5, and 10 mm. The spacing of the third or fourth edges from the outermost edge 43 of the nostril can be the same or different. In various embodiments, the nose opening 114 can have a first edge that is spaced about 0 mm to about 10 mm from the base of the columella 44. In various embodiments, the nose opening 114 can have a second edge that is disposed on a portion of the tip 38 of the nose. For example, the second edge 118 can be arranged such that is extends across the top of the first and second nostrils 40, 42, and in the area of the nostril is spaced about 0 to about 10 mm from the upper most point 49 of the respective nostril 40, 42. For example, the spacing can be about 0 mm to about 10 mm, about 0 mm to about 5 mm, about 2 mm to about 6 mm, about 1 mm to about 5 mm, about 3 mm to about 5 mm Other suitable spacings can include, for example, about 0, 1, 1.5, 2, 2.5, 3, 3.5, 4, 4.5, 5, 5.5, 6, 6.5, 7, 7.5, 8, 8.5, 9, 9.5, and 10 mm. The spacing of the second edge 118 from the first and second nostrils 40, 42 can be the same in the region of each nostril or different in the region of each nostril.

In embodiments, a nose opening 114 can be defined by determining a position of an outermost edge 43 of each of first and second nostrils 40, 42, setting a first nose anchor point about 0 mm to about 10 mm from the outermost edge 43 of the first nostril 40, setting a second nose anchor point about 0 mm to about 10 mm from the outermost edge 43 of the second nostril 42, and defining a nose opening 114 having side edges 120, 122 that intersect with the first and second nose anchor points. In various embodiments, the method can include or further includes determining a position of the base of the columella 44, determining a position of the tip 38 of the nose, setting a third nose anchor point about 0 mm to about 10 mm from the position of the base of the columella 44 and a fourth nose anchor point 0 mm to about 10 mm from the position of the tip 38 of the nose, and defining a nose opening 114 to have a circumferential edges that intersects with each of the first, second, third, and fourth anchor points. In various embodiments, the method can include or further includes determining an uppermost point 49 of at least one of the first and second nostrils 40, 42;

setting a fifth anchor point about 0 to about 10 mm from one of the uppermost points of the first and second nostrils 40, 42, and defining the mask 100 to have a nose opening 114 with top and bottom edges 116, 118 that intersect with the third and fifth anchor points, respectively. In various embodiments, the fifth anchor point can be the uppermost one of the uppermost point 49 of the first and second nostrils 40, 42. In various embodiments, the fifth anchor point can be the uppermost point of the first nostril 40 and a fifth anchor point can be defined at the upper most point of the second nostril 42. In various embodiments, the method can include determining the uppermost point of each of the first and second nostrils 40, 42 and defining fifth and sixth anchor points at each of the uppermost points and defining a nose opening 114 having a second edge that intersects with the first, second, fifth, and sixth nose anchor points. Optionally, the second edge 118 in such embodiments can intersect with the fourth nose anchor point. In various embodiments, the nose opening 114 can be defined such that the edges of the opening 114 interest with two anchor points, three anchor points, four anchor points, five anchor points, six anchor points, or more. Further, the nose hole may be a single nose opening, one opening per nostril, or may be a series of holes or other treatments to enable air permeability in the defined region of the nose to allow the user to breathe comfortably while wearing the mask.

Figure 13:
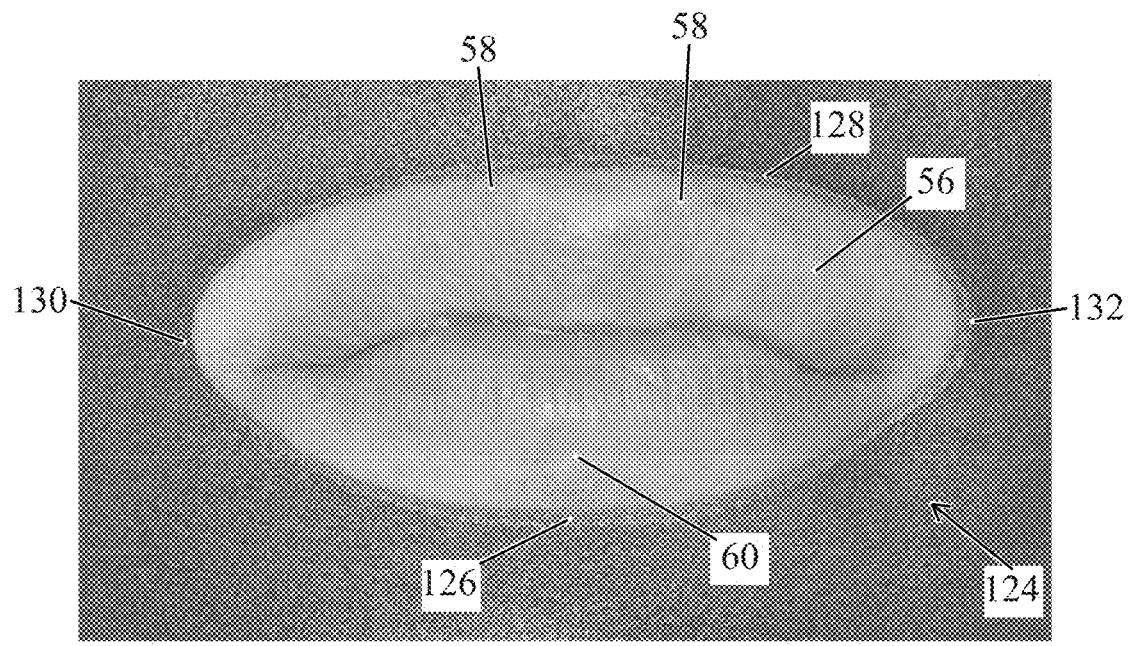
FIG. 13 is a photograph of a mouth region of a human face, showing a face mask fitted to the mouth region and having a mouth opening in accordance with embodiments of the disclosure.

In accordance with various embodiments, the mask 100 can include or further include a mouth opening 124. The mouth opening 124 can be, for example, defined to allow for close coverage of the mouth region 50 without interfering with movement of the lips 52, 54 and/or overlapping or covering the lips 52, 54. Referring to FIG. 13, the mouth opening 124 can have a height HMO extending between first and second edges 126, 128, and a width $W_{MO}$ extending between first and second corners 130, 132. In various embodiments, the mask 100 can have a mouth opening 124 defined such that the first edge 126 is spaced about 0 mm to about 10 mm from the lower point 60 of the vermillion border 56 on the lower lip 54. For example, the spacing can be about 0 mm to about 10 mm, about 0 mm to about 5 mm, about 2 mm to about 6 mm, about 1 mm to about 5 mm, about 3 mm to about 5 mm Other suitable spacings can include, for example, about 0, 1, 1.5, 2, 2.5, 3, 3.5, 4, 4.5, 5, 5.5, 6, 6.5, 7, 7.5, 8, 8.5, 9, 9.5, and 10 mm. In various embodiments the mask 100 can have a mouth opening 124 defined such that the second edge 128 is spaced about 0 mm to about 10 mm from the upper point 58 of the vermillion border 56 on the upper lip 52. For example, the spacing can be about 0 mm to about 10 mm, about 0 mm to about 5 mm, about 2 mm to about 6 mm, about 1 mm to about 5 mm, about 3 mm to about 5 mm Other suitable spacings can include, for example, about 0, 1, 1.5, 2, 2.5, 3, 3.5, 4, 4.5, 5, 5.5, 6, 6.5, 7, 7.5, 8, 8.5, 9, 9.5, and 10 mm. In various embodiments, the mask 100 can have a mouth opening 124 defined such that the first and second corners 130, 132 (also referred to as first and second edges or sides) are spaced about 0 mm to about 10 mm from the first and second corners 62, 64 of the mouth 62, 64. For example, the spacing can be about 0 mm to about 10 mm, about 0 mm to about 5 mm, about 2 mm to about 6 mm, about 1 mm to about 5 mm, about 3 mm to about 5 mm. Other suitable spacings can include, for example, about 0, 1, 1.5, 2, 2.5, 3, 3.5, 4, 4.5, 5, 5.5, 6, 6.5, 7, 7.5, 8, 8.5, 9, 9.5, and 10 mm. The spacing of the first and second corners 130, 132 of the mouth opening 124 can have the same spacing from the respective corner 62, 64 of the mouth or can have different spacing.

In accordance with various embodiments, the methods of making a mask 100 can include or further include defining a mouth opening 124 by determining a position of an upper point 58 of the vermillion border 56; determining a position of a lower point 60 of the vermillion border 56, setting a first lip anchor point about 0 mm to about 10 mm from the upper point 58 of the vermillion border 56, setting a second lip anchor point about 0 mm to about 10 mm from the lower point 60 of the vermillion border 56, and defining a mask 100 having a mouth opening 124 with a first edge 126 that intersects with the first lip anchor point and a second edge 128 that intersects with the second lip anchor point. A mouth can include two upper points 58 of the vermillion border 56 as illustrated in FIG. 13. In embodiments, the method can include determining a position of each of the upper points 58 and two first lip anchor points can be set at about 0 m to about 10 mm from each of the upper points 58 of the vermillion border. The spacing of the first anchor points can be the same or can be different. In other embodiments, the method can include determining a position of the upper most one of the upper points 58. In various embodiments, the method can include or further include determining position of each of the first and second corners 62, 64 of the mouth, setting a third lip anchor point about 0 mm to about 10 mm from the first corner 62, setting a fourth lip anchor point about 0 mm to about 10 mm from the second corner 64, and defining a mouth opening 124 having a first edge that intersects the first, third, and fourth anchor points, and a second edge that intersects the second, third, and fourth anchor points.

In any of the embodiments of a method of the disclosure defining a nose opening 114 and/or a mouth opening 124, a Bezier curve or any other connector can be used as described above with respect to the eye opening 102.

In accordance with any of the embodiments of the disclosure, the mask 100 can be two-dimensional mask 100, or can be three-dimensional masks 100. Mask 100 can be made using any suitable technique in which the openings features as defined by the methods disclosed herein can be incorporated. For example, the methods in accordance with embodiments of the disclosure can be used to define cutting paths for cutting openings into preformed mask 100 materials or into flat mask materials such as substrate masks. In accordance with embodiments, laser cutting can be used for cutting the defined cutting paths. Additionally or alternative, in embodiments, custom-defined molds may be used to define a gel mask having one or more openings in accordance with embodiments of the disclosure. For example, the methods in accordance with embodiments of the disclosure can be used to define an opening region in a digital geometric representation of a three-dimensional mask 100 to be created by digital printing or other molding techniques. For example, mask 100 can be digitally created using techniques such as described in any one or more of U.S. Patent Application Publication Nos. 2017/008566, 2017/0354805, and 2017/0354806, the respective disclosures of which are incorporated herein by reference. The process to define one or more openings may be manual or partial or fully automated and may use various algorithms. Further, perspective angle of the image may be accounted for and or measured to ensure data quality. Perspective angle corrections may use comparisons of multiple images, phone sensor data, by guiding a user during acquiring images and any digital data, or other means.

Masks 100 having openings made in accordance with the methods of embodiments of the disclosure can include any suitable active, cosmetic, or therapeutic agent to be applied to the face of the user. For example, active, therapeutic, and/or cosmetic agents can include active ingredients, carriers, chassis, emulsions, hydrogels, adhesives, process aides (such as thickeners, rheology modifiers, etc.). Active agents may further comprise a release layer to help active agents transfer from the applicator to the target surface. Active agents may include adhesive materials, active chemical agents, absorbent materials such as absorbent gel materials or absorbent foam materials placed according to either the diagnostic scan or relative to identifiable features. As an example, it may be desirable to dispose an absorbent foam material along cheekbones, brow or nose of a scanned user's facial mask 100, the disposition sites may be determined according to the geometry of the representation rather than according to the diagnostic scan of the user. Active agents may be in one or more physical forms, including but not limited to: foams, liquids, powders, films, fibers, creams, gels, hydrogels, encapsulated active agents, solids, combinations of these forms and other forms. Some examples of active agents include but are not limited to: moisturizer, anti-aging, anti-wrinkle, skin tone control, anti-irritation, sensates (e.g. menthol), heating or cooling chemistries, skin tightening, hair removal, hair regrowth, fungicide, antibacterial, antiviral, surfactants, cleaning agents, copper ion eluting (such as from Cupron of Richmond, Va.), antioxidants, vitamins, sunscreen, rejuvenation agents, wound healing agents, sebum management agents, astringents, exfoliates, anti-inflammatory, leave on, overnight, dry skin, itchy skin, cracked skin, peptides, acne, scar treatments, sore muscles treatments, medicaments including pharmacological actives to treat disease states or other acute or chronic issues such as eczema, rashes, acne, cancer, cold sore, Psoriasis, Rosacea, Vitiligo, warts, Herpes, fungal infection, Actinic Keratosis, ulcers, shingles, poison ivy, and insect bites. Further, the medicaments, including pharmacological actives, can go beyond topical effect and be designed for transdermal delivery of an active into the bloodstream or other internal tissue. Examples of therapies, both prescribed and un-prescribed include: nicotine, Botox, and hormone supplements.

Exemplary active agents for cosmetic changes to the target structure include: hydrating agents, acne treating agent, anti-aging agents, anti-wrinkle agents, matte-finish compounds, under-eye hydrating agents, anti-oil agents, primer, lipstick, lip gloss, lip liner, lip plumper, lip balm, lip conditioner, lip primer, lip boosters, concealer, foundation, powder, rouge, blush, blusher, contour powder/creams, highlight, bronzer, mascara, eyeliner, and setting materials, scents, perfume or fragrance compositions (e.g. essential oils).

In one embodiment, the inclusion of one or more scents, perfume or fragrance compositions may be applied to the mask 100 for subsequent deposition to the face. However, a portion, or all, of the included one or more scents, perfume or fragrance compositions may act as experience agents. The experience agent provides a smell in the environs of the mask 100 when in use. For example, the smell provided by a fragrance to suggest outdoor flower garden aroma may be desirable when applying cosmetic agents to the face of a consumer/wearer. Experiential agents need not necessarily be located on the target structure contact surface of the mask 100. The agents may be located in a region not in contact with the target structure, such as on a non-contacting portion of the application side of the applicator or anywhere on any applicator side that is non-contacting to the target structure. The experience agent may be selected to accompany a selected appearance feature.

EXAMPLES

Example 1

An eye opening 102 cutting path was created digital using a method in accordance with the disclosure. FIGS. 7A and 7B illustrate the mask 100 formed from the developed custom eye opening 102.

Digital data corresponding to a three-dimensional mesh of a face was loaded into Blender graphics program. The mesh of the face was aligned flat, with the nose pointing up in the positive Z direction, the chin and forehead at approximately the same Z height, and the left and right cheeks at approximately the same Z height. The face mesh was oriented to a top down orthographic view. The face mesh was viewed with and without captured texture/color information to provide complementary information on where the reference points are located.

Four anchor points were selected on the digital geometric representation of the face presented as a mesh. The lower eye region bound 66 was defined at the lowest extent of the upper eyelashes 24 when the eye is closed. A first anchor point 104 was set to be about 3.5 mm below the lower eye region bound 66. The upper eye region bound 68 was defined at the peak point 34 of an arc of concavity of the upper eyelid 16. A second anchor point 106 was set to be about 3.5 mm above the upper eye region bound 68. The position of the medial and lateral canthus 26, 28 was determined on the mesh and third and fourth anchor points 110, 112 were set to be about 3.5 mm outbound (relative to the eyeball 12) from the medial and lateral canthus 26, 28, respectively. The mesh was manipulated at various angles in the software to help define the anchor points.

A Bezier curve was overlaid over the digital geometric representation 2 cm floating above the digital geometric representation of the eye with the four anchor points. The handles for each of the anchor points was adjusted in succession until the Bezier curve followed the points of lowest curvature tracing the underlying eyeball 12. Once achieved, the Bezier curve defined the eye opening 102.

The Bezier curve converted to a mesh and exported as a DXF file to be used in an XY laser cutter. The mesh of the Bezier curves as generated to have approximately 50 segments. The eye openings 102 were then cut using the laser cutter into an already formed mask, thereby forming the eye openings 102 shown in FIGS. 7A and 7B.

Example 2

A face mesh having eye-openings 102 defined therein in accordance with a method of the disclosure was generated for direct printing of the face mask having the eye openings formed upon printing.

Digital data corresponding to a three-dimensional mesh of a face was loaded into Blender graphics program. The mesh of the face was aligned flat, with the nose pointing up in the positive Z direction, the chin and forehead at approximately the same Z height, and the left and right cheeks at approximately the same Z height. The face mesh was oriented to a top down orthographic view. The face mesh was viewed with and without captured texture/color information to provide complementary information on where the reference points are located.

Four anchor points were selected on the digital geometric representation of the face presented as a mesh. The lower eye region bound 66 was defined at the lowest extent of the upper eyelashes 24 when the eye is closed. A first anchor point 104 was set to be about 3.5 mm below the lower eye region bound 66. The upper eye region bound 68 was defined at the peak point 34 of an arc of concavity of the upper eyelid 16. A second anchor point 106 was set to be about 3.5 mm above the upper eye region bound 68. The position of the medial and lateral canthus 26, 28 was determined on the mesh and third and fourth anchor points 110, 112 set to be about 3.5 mm outbound (relative to the eyeball 12) from the medial and lateral canthus 26, 28, respectively. The mesh was manipulated at various angles in the software to help define the anchor points.

A Bezier curve was overlaid over the digital geometric representation 2 cm floating above the digital geometric representation of the eye with the four anchor points. The handles for each of the anchor points were adjusted in succession until the Bezier curve followed the points of lowest curvature tracing the underlying eyeball 12. Once achieved, the Bezier curve defined the eye opening 102.

The Bezier curved was then used to create an eye opening 102 in a face mesh digitally and subsequently direct print a mask with the defined eye openings removed upon printing. The Bezier curve was converted into a mesh with approximately 50 segments and extruded in the negative Z direction to the extent that it intersects and passes through the face mesh surface. In particular, the Bezier curve was originally 20 mm above the eye of the face mesh and extruded −50 mm to intersect the face mesh. The face mesh is then selected and a Boolean difference with the extruded mesh eye opening cut path was used to remove the eye region within the cut path to leave the defined eye opening in the face mesh. The resulting face mesh having the eye openings removed therefrom can then be exported for direct printing.

Example 3

A nose opening 114 cutting path was created digitally using a method in accordance with the disclosure. FIG. 12 illustrates the mask 100 formed from the developed custom nose opening 114.

Digital data corresponding to a three-dimensional mesh of a face was loaded into Blender graphics program. The mesh of the face was aligned flat, with the nose pointing up in the positive Z direction, the chin and forehead at approximately the same Z height, and the left and right cheeks at approximately the same Z height. The face mesh was oriented to a top down orthographic view. The face mesh was viewed with and without captured texture/color information to provide complementary information on where the reference points are located.

Four anchor points were selected on the digital geometric representation of the face presented as a mesh. Left and right anchor points 120 and 122 are set as the midpoint of the outer nostril walls on either side 46 and 48. Upper anchor point 118 is set as the center of the nose above the columella, 3 mm above the highest point of the nostril 49. Lower anchor point 116 is set as the center of the nose below the columella, 3 mm below the base of the columella 44. The mesh was manipulated at various angles in the software to help define the anchor points.

A Bezier curve was overlaid over the digital geometric representation 2 cm floating above the digital geometric representation of the nose with the four anchor points. The handles for each of the anchor points were adjusted in succession until the Bezier curve followed the central line of the nostril sidewalls 46, 48. Once achieved, the Bezier curve defined the nose opening 114.

The Bezier curve converted to a mesh and exported as a DXF file to be used in an XY laser cutter. The mesh of the Bezier curves as generated to have approximately 50 segments. The nose opening 114 was then cut using the laser cutter into a mask material, thereby forming the nose opening 114 shown in FIG. 12.

Example 4

A face mesh having a nose opening 114 defined therein in accordance with a method of the disclosure was generated for direct printing of the face mask having the nose openings formed upon printing.

Digital data corresponding to a three-dimensional mesh of a face was loaded into Blender graphics program. The mesh of the face was aligned flat, with the nose pointing up in the positive Z direction, the chin and forehead at approximately the same Z height, and the left and right cheeks at approximately the same Z height. The face mesh was oriented to a top down orthographic view. The face mesh was viewed with and without captured texture/color information to provide complementary information on where the reference points are located.

Four anchor points were selected on the digital geometric representation of the face presented as a mesh. Left and right anchor points 120 and 122 are set as the midpoint of the outer nostril walls on either side 46 and 48. Upper anchor point 118 is set as the center of the nose above the columella, 3 mm above the highest point of the nostril 49. Lower anchor point 116 is set as the center of the nose below the columella, 3 mm below the base of the columella 44. The mesh was manipulated at various angles in the software to help define the anchor points.

A Bezier curve was overlaid over the digital geometric representation 2 cm floating above the digital geometric representation of the nose with the four anchor points. The handles for each of the anchor points were adjusted in succession until the Bezier curve followed the central line of the nostril sidewalls 46, 48. Once achieved, the Bezier curve defined the nose opening 114.

The Bezier curved was then used to create a nose opening 114 in a face mesh digitally and subsequently direct print a mask with the defined nose opening removed upon printing. The Bezier curve was converted into a mesh with approximately 50 segments and extruded in the negative Z direction to the extent that it intersects and passes through the face mesh surface. In particular, the Bezier curve was originally 20 mm above the nose of the face mesh and extruded −50 mm to intersect the face mesh. The face mesh is then selected and a Boolean difference with the extruded mesh nose opening cut path was used to remove the nose region within the cut path to leave the defined nose opening in the face mesh. The resulting face mesh having the nose opening removed therefrom can then be exported for direct printing.

Example 5

A mouth opening 124 cutting path was created digitally using a method in accordance with the disclosure. FIG. 13 illustrates the mask 100 formed from the developed custom mouth opening 124.

Digital data corresponding to a three-dimensional mesh of a face was loaded into Blender graphics program. The mesh of the face was aligned flat, with the mouth pointing up in the positive Z direction, the chin and forehead at approximately the same Z height, and the left and right cheeks at approximately the same Z height. The face mesh was oriented to a top down orthographic view. The face mesh was viewed with and without captured texture/color information to provide complementary information on where the reference points are located.

Four anchor points were selected on the digital geometric representation of the face presented as a mesh. Left and right anchor points 130 and 132 are set as 3 mm out from the corners of the mouth 62 and 64. Upper anchor point 128 is set as 3 mm above the upper vermillion border 58 in the center of the mouth. Lower anchor point 126 is set as 3 mm below the lower vermillion border 60 in the center of the mouth. The mesh was manipulated at various angles in the software to help define the anchor points.

A Bezier curve was overlaid over the digital geometric representation 2 cm floating above the digital geometric representation of the mouth with the four anchor points. The handles for each of the anchor points was adjusted in succession until the Bezier curve generally followed vermillion border at an offset of at least 3 mm Once achieved, the Bezier curve defined the mouth opening 124.

The Bezier curve converted to a mesh and exported as a DXF file to be used in an XY laser cutter. The mesh of the Bezier curves as generated to have approximately 50 segments. The mouth opening 124 was then cut using the laser cutter into a mask material, thereby forming the mouth opening 124 shown in FIG. 13.

Example 6

A face mesh having a mouth opening 124 defined therein in accordance with a method of the disclosure was generated for direct printing of the face mask having the mouth openings formed upon printing.

Digital data corresponding to a three-dimensional mesh of a face was loaded into Blender graphics program. The mesh of the face was aligned flat, with the mouth pointing up in the positive Z direction, the chin and forehead at approximately the same Z height, and the left and right cheeks at approximately the same Z height. The face mesh was oriented to a top down orthographic view. The face mesh was viewed with and without captured texture/color information to provide complementary information on where the reference points are located.

Four anchor points were selected on the digital geometric representation of the face presented as a mesh. Left and right anchor points 130 and 132 are set as 3 mm out from the corners of the mouth 62 and 64. Upper anchor point 128 is set as 3 mm above the upper vermillion border 58 in the center of the mouth. Lower anchor point 126 is set as 3 mm below the lower vermillion border 60 in the center of the mouth. The mesh was manipulated at various angles in the software to help define the anchor points.

A Bezier curve was overlaid over the digital geometric representation 2 cm floating above the digital geometric representation of the mouth with the four anchor points. The handles for each of the anchor points was adjusted in succession until the Bezier curve generally followed vermillion border at an offset of at least 3 mm. Once achieved, the Bezier curve defined the mouth opening 124.

The Bezier curved was then used to create a mouth opening 124 in a face mesh digitally and subsequently direct print a mask with the defined mouth opening removed upon printing. The Bezier curve was converted into a mesh with approximately 50 segments and extruded in the negative Z direction to the extent that it intersects and passes through the face mesh surface. In particular, the Bezier curve was originally 20 mm above the mouth of the face mesh and extruded −50 mm to intersect the face mesh. The face mesh is then selected and a Boolean difference with the extruded mesh mouth opening cut path was used to remove the mouth region within the cut path to leave the defined mouth opening in the face mesh. The resulting face mesh having the mouth opening removed therefrom can then be exported for direct printing.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a face mask for a face of a human user, comprising:
    a) determining on a digital geometric representation of the face including at least one eye:
        a position of a medial canthus,
        a position of a lateral canthus,
        a lower eye region bound, and
        an upper eye region bound;
    b) setting a first anchor point 1 mm to 10 mm outboard from the medial canthus;
    c) setting a second anchor point 1 mm to 10 mm outboard from the lateral canthus;
    d) setting a third anchor point spaced 0 mm to 10 mm below a lower eye region bound;
    e) setting a fourth anchor point spaced 0 mm to 10 mm above the upper eye region bound; and
    f) defining at least one eye opening having a first edge defined by a first curve connecting the first, third, and second anchor points, and a second edge defined by a second curve connecting the first, fourth, and second anchor points; and
    g) creating the face mask having the defined at least one eye opening;
    wherein the lower eye region bound is the one of a lowest extent of one or more lower eyelashes, a lower bound of an eyeball, and a lowest extent of one or more upper eyelashes, having the greatest distance from a lower lid margin of the at least one eye.

2. The method of claim 1, wherein the first and second curves are Bezier curves.

3. The method of claim 1, wherein the digital geometric representation of the face includes first and second eyes, and the method comprises repeating steps a) through g) for each of the first and second eyes to define first and second eye openings, respectively.

4. The method of claim 1, wherein creating the face mask comprises exporting a first set of data representing the first curve and a second set of data representing the second curve to a device arranged to cut a pattern corresponding to the first and second curves in a mask material.

5. The method of claim 4, wherein the first and second sets of data each comprises first and second series of segments representing the first and second curves, respectively.

6. The method of claim 5, wherein the first and second series of segments each comprise 30 to 100 segments.

7. The method of claim 1, further comprising defining a registration feature of the mask, such that when worn, the registration feature orients the eye opening relative to the eye.

8. The method of claim 7, wherein the registration feature is a feature covering one or more of a nose, a chin, and a jaw section of the face when the mask is worn.

9. The method of claim 7, wherein a registration feature is defined using a digital representation of the face including the at least one eye and the registration area.

10. The method of claim 1, wherein the mask is a two dimensional substrate mask.

11. The method of claim 1, wherein the mask is a three dimensional mask.

12. The method of claim 1, wherein the upper eye region bound is determined by locating an upper bound of the eyeball as determined by a peak point of an arc of concavity in an upper eyelid of the at least one eye when the eye is closed.

13. A method of making a face mask for a face of a human user, comprising:
 a) determining on a digital geometric representation of the face including at least one eye:
  a position of a medial canthus,
  a position of a lateral canthus,
  a lower eye region bound, and
  an upper eye region bound;
 b) setting a first anchor point 1 mm to 10 mm outboard from the medial canthus;
 c) setting a second anchor point 1 mm to 10 mm outboard from the lateral canthus;
 d) setting a third anchor point spaced 0 mm to 10 mm below a lower eye region bound;
 e) setting a fourth anchor point spaced 0 mm to 10 mm above the upper eye region bound; and
 f) defining at least one eye opening having a first edge defined by a first curve connecting the first, third, and second anchor points, and a second edge defined by a second curve connecting the first, fourth, and second anchor points; and
 g) creating the face mask having the defined at least one eye opening;
 wherein forming the face mask comprises digitally extruding a first set of data representing the first curve and a second set of data representing the second curve in a negative Z direction such that it intersects a three dimensional digital geometric representation of the face mask; digitally removing a region of the digital geometric representation of the face mask disposed between the first and second curves thereby providing a digital geometric representation of a face mask having the at least one eye opening; and exporting the digital geometric representation of the face mask having the at least one eye opening for direct printing of the face mask with the at least one eye opening.

14. The method of claim 13, wherein the first and second curves are Bezier curves.

15. The method of claim 13, wherein the digital geometric representation of the face includes first and second eyes, and the method comprises repeating steps a) through g) for each of the first and second eyes to define first and second eye openings, respectively.

16. The method of claim 13, wherein creating the face mask comprises exporting a first set of data representing the first curve and a second set of data representing the second curve to a device arranged to cut a pattern corresponding to the first and second curves in a mask material.

17. The method of claim 16, wherein the first and second sets of data each comprises first and second series of segments representing the first and second curves, respectively.

18. The method of claim 17, wherein the first and second series of segments each comprise 30 to 100 segments.

19. A method of making a face mask for a face of a human user, comprising:
 a) determining on a digital geometric representation of the face including at least one eye:
  a position of a medial canthus,
  a position of a lateral canthus,
  a lower eye region bound, and
  an upper eye region bound;
 b) setting a first anchor point 1 mm to 10 mm outboard from the medial canthus;
 c) setting a second anchor point 1 mm to 10 mm outboard from the lateral canthus;
 d) setting a third anchor point spaced 0 mm to 10 mm below a lower eye region bound;
 e) setting a fourth anchor point spaced 0 mm to 10 mm above the upper eye region bound; and
 f) defining at least one eye opening having a first edge defined by a first curve connecting the first, third, and second anchor points, and a second edge defined by a second curve connecting the first, fourth, and second anchor points; and
 g) creating the face mask having the defined at least one eye opening;
 wherein the lower eye region bound is determined by locating a position of one or more of a lowest extent of one or more lower eyelashes of the at least one eye when the eye is open, a lower bound of an eyeball as determined by a peak point of an arc of concavity in the lower eyelid of the at least one eye when the eye is closed, and a lowest extent of one or more upper eyelashes of the at least one eye when the eye is closed.

20. The method of claim 19, wherein the first and second curves are Bezier curves.

* * * * *